United States Patent
Avkin-Nachum

(10) Patent No.: US 9,701,960 B2
(45) Date of Patent: *Jul. 11, 2017

(54) SIRNA COMPOUNDS COMPRISING TERMINAL SUBSTITUTIONS

(71) Applicant: Quark Pharmaceuticals, Inc., Fremont, CA (US)

(72) Inventor: Sharon Avkin-Nachum, Nes Zionna (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/451,233

(22) Filed: Aug. 4, 2014

(65) Prior Publication Data

US 2015/0152412 A1 Jun. 4, 2015

Related U.S. Application Data

(62) Division of application No. 13/511,111, filed as application No. PCT/US2010/058123 on Nov. 25, 2010, now Pat. No. 8,796,239.

(60) Provisional application No. 61/264,668, filed on Nov. 26, 2009, provisional application No. 61/295,721, filed on Jan. 17, 2010, provisional application No. 61/372,072, filed on Aug. 9, 2010.

(51) Int. Cl.
   C12N 15/11 (2006.01)
   C12N 15/113 (2010.01)

(52) U.S. Cl.
   CPC .......... *C12N 15/113* (2013.01); *C12N 15/111* (2013.01); *C12N 2310/14* (2013.01); *C12N 2310/141* (2013.01); *C12N 2310/317* (2013.01); *C12N 2310/321* (2013.01); *C12N 2310/333* (2013.01); *C12N 2310/344* (2013.01); *C12N 2320/52* (2013.01)

(58) Field of Classification Search
   None
   See application file for complete search history.

(56) References Cited

U.S. PATENT DOCUMENTS

| | | | |
|---|---|---|---|
| 5,898,031 A | 4/1999 | Crooke | |
| 5,998,203 A | 12/1999 | Matulic-Adamic et al. | |
| 6,107,094 A | 8/2000 | Crooke | |
| 6,117,657 A | 9/2000 | Usman et al. | |
| 6,235,886 B1 | 5/2001 | Manoharan et al. | |
| 6,251,666 B1 | 6/2001 | Beigelman | |
| 6,506,559 B1 | 1/2003 | Fire et al. | |
| 6,586,238 B1 | 7/2003 | Matulic-Adamic et al. | |
| 6,602,858 B2 | 8/2003 | Beigelman | |
| 7,056,704 B2 | 6/2006 | Tuschl et al. | |
| 7,078,196 B2 | 7/2006 | Tuschl et al. | |
| 7,452,987 B2 | 11/2008 | Giese et al. | |
| 7,459,547 B2 | 12/2008 | Zamore et al. | |
| 7,732,593 B2 | 6/2010 | Zamore et al. | |
| 7,750,144 B2 | 7/2010 | Zamore et al. | |
| 7,772,203 B2 | 8/2010 | Zamore et al. | |
| 7,812,002 B2 | 10/2010 | Feinstein | |
| 7,893,245 B2 | 2/2011 | Giese et al. | |
| 8,090,542 B2 | 1/2012 | Khvorova et al. | |
| 8,097,710 B2 | 1/2012 | Baulcombe et al. | |
| 2003/0027783 A1 | 2/2003 | Zernicka-Goetz et al. | |
| 2003/0108923 A1 | 6/2003 | Tuschl et al. | |
| 2004/0063654 A1 | 4/2004 | Davis et al. | |
| 2004/0192626 A1 | 9/2004 | McSwiggen et al. | |
| 2004/0229266 A1 | 11/2004 | Tuschl et al. | |
| 2004/0265839 A1 | 12/2004 | Mello et al. | |
| 2005/0004064 A1 | 1/2005 | Tei et al. | |
| 2005/0020525 A1 | 1/2005 | McSwiggen et al. | |
| 2005/0037988 A1 | 2/2005 | Zamore et al. | |
| 2005/0042647 A1 | 2/2005 | Baker et al. | |
| 2005/0080246 A1 | 4/2005 | Allerson et al. | |
| 2005/0181382 A1 | 8/2005 | Zamore et al. | |
| 2005/0223427 A1 | 10/2005 | Leake et al. | |
| 2005/0233342 A1 | 10/2005 | Manoharan et al. | |
| 2005/0255487 A1 | 11/2005 | Khvorova et al. | |
| 2006/0058266 A1 | 3/2006 | Manoharan et al. | |
| 2006/0069056 A1 | 3/2006 | Feinstein et al. | |
| 2006/0217329 A1 | 9/2006 | Feinstein | |
| 2006/0241072 A1 | 10/2006 | Baker | |
| 2007/0031844 A1 | 2/2007 | Khvorova et al. | |
| 2007/0032441 A1 | 2/2007 | McSwiggen et al. | |
| 2007/0185047 A1 | 8/2007 | Bhat et al. | |
| 2007/0259827 A1 | 11/2007 | Aronin et al. | |
| 2009/0162365 A1 | 6/2009 | Feinstein et al. | |

(Continued)

FOREIGN PATENT DOCUMENTS

WO  WO 00/44895 A1  8/2000
WO  WO 00/44914 A1  8/2000

(Continued)

OTHER PUBLICATIONS

Aarzguioui et al. (2003). Tolerance for mutations and chemical modifications in a siRNA. *Nucleic Acids Research*, 31(2), 589-595.
Barik (2005). Silence of the transcripts; RNA interference in medicine. *J Mol Med*, 83, 764-773.
Bass (2001). The short answer. *Nature*, 411, 428-429.
Braasch et al. (2003). RNA interference in mammalian cells by chemically-modified RNA. *Biochemistry*, 42, 7967-7975.
Caplen et al. (2001). Specific inhibition of gene expression by small double-stranded RNAs in invertebrate and vertebrate systems. *Proc Natl Acad Sci*, 98(17), 9742-9747.
Chakraborty (2007). Potentiality of small interfering RNAs (siRNA) as recent therapeutic targets for gene-silencing. *Current Drug Targets*, 8(3), 469-482.

(Continued)

*Primary Examiner* — Kate Poliakova-Georgantas
(74) *Attorney, Agent, or Firm* — Nutter McClennen & Fish LLP; Konstantin Linnik

(57) ABSTRACT

The invention relates to modified siRNA compounds which down-regulate target gene expression, to pharmaceutical compositions comprising such compounds and to methods of treating and/or preventing the incidence or severity of various diseases or conditions associated with the genes and/or symptoms associated with such diseases or conditions.

18 Claims, 10 Drawing Sheets

(56) References Cited

U.S. PATENT DOCUMENTS

| | | |
|---|---|---|
| 2009/0209626 A1 | 8/2009 | Khvorova et al. |
| 2010/0184826 A1 | 7/2010 | Zamore et al. |
| 2010/0184827 A1 | 7/2010 | Zamore et al. |
| 2010/0184828 A1 | 7/2010 | Zamore et al. |
| 2010/0292301 A1 | 11/2010 | Feinstein et al. |
| 2010/0317105 A1 | 12/2010 | Zamore et al. |
| 2011/0112168 A1 | 5/2011 | Feinstein et al. |
| 2011/0178157 A1 | 7/2011 | Jin et al. |
| 2012/0052487 A9 | 3/2012 | Khvorova et al. |

FOREIGN PATENT DOCUMENTS

| | | |
|---|---|---|
| WO | WO 01/88836 A2 | 9/2001 |
| WO | WO 02/44321 | 6/2002 |
| WO | WO 02/055693 A2 | 7/2002 |
| WO | WO 03/064621 A2 | 8/2003 |
| WO | WO 03/070918 A2 | 8/2003 |
| WO | WO 03/074654 A2 | 9/2003 |
| WO | WO 2004/002402 | 1/2004 |
| WO | WO 2004/015107 | 2/2004 |
| WO | WO 2004/111191 A2 | 12/2004 |
| WO | WO 2005/102275 | 11/2005 |
| WO | WO 2006/023544 | 3/2006 |
| WO | WO 2007/084684 | 7/2007 |
| WO | WO 2007/087451 A2 | 8/2007 |
| WO | WO 2007/107789 | 9/2007 |
| WO | WO 2007/141796 | 12/2007 |
| WO | WO 2008/050329 | 5/2008 |
| WO | WO 2009/090639 | 7/2008 |
| WO | WO 2008/106102 | 9/2008 |
| WO | WO 2008/152636 | 12/2008 |
| WO | WO 2009/001359 | 12/2008 |
| WO | WO 2010/048352 A2 | 4/2010 |
| WO | WO 2012/078536 | 6/2012 |

OTHER PUBLICATIONS

Chiu and Rana (2002). RNAi in human cells: basic structural and function features of small interfering RNA. *Molecular Cell*, 10, 549-561.

Chiu and Rana (2003). siRNA function in RNAi: a chemical modification analysis. *RNA*, 9(9), 1034-1048.

Czauderna et al. (2003). Structural variations and stabilising modifications of synthetic siRNAs in mammalian cells. *Nucleic Acids Research*, 31(11), 2705-2716.

Ding et . (2008). Asymmetrically designed siRNAs and shRNAs enhance the strand specificity and efficacy in RNAi. *J RNAi Gene Silenc*, 4(1), 269-280.

Du et al. (2005). A systematic analysis of the silencing effects of an active siRNA at all single-nucleotide mismatched target sites. *Nucleic Acids Research*, 33(5), 1671-1677.

Elbashir et al. (2001). RNA interference is mediated by 21-and 22-nucleotide RNAs. *Genes & Development*, 15, 188-200.

Elbashir et al. (2001). Functional anatomy of siRNAs for mediating efficient RNAi in *Drosophila melanogaster* embryo lysate. *EMBO Journal*, 20(23), 6877-6888.

Elbashir et al. (2001). Duplexes of 21-nucleotide RNAs mediate RNA interference in cultured mammalian cells. *Nature 411*, 494-498.

Fire et al. (1998). Potent and specific genetic interference by double-stranded RNA in Caenorhabditis elegans. *Nature*, 391, 806-8.

Hohjoh (2003). Enhancement of RNAi activity by improved siRNA duplexes. *FEBS Letters*, 557, 193-198.

Holen et al. (2002). Positional effects of short interfering RNAs targeting the human coagulation trigger tissue factor. *Nucleic Acids Research*, 30(8), 1757-1766.

Huang et al. (2009). Profiling of mismatch discrimination in RNAi enabled rational design of allele-specific siRNAs. *Nucleic Acids Research*, 37(22), 7560-7569.

Khvorova et al. (2003). Functional siRNAs and miRNAs exhibit strand bias. *Cell*, 115, 209-216.

Kini and Walton (2009), Effect siRNA terminal mismatches on TRBP and Dicer binding and silencing efficacy. *FEBS Journal*, 276(22), 6576-6585.

Kurreck (2006). siRNA efficiency: structure or sequence—that is the question. *J Biomed Biotechnol*, 2006, 83757.

Mahato et al. (2005) Modulation of gene expression by antisense and antigene oligodeoxynucleotides and small interfering RNA. *Expert Opinion on Drug Delivery*, 2(1), 3-28.

McManus and Sharp (2002). Gene silencing in mammals by small interfering RNAs. *Nature Reviews Genetics*, 3, 737-747.

Prakash et al. (2005). Positional effect of chemical modifications on short interference RNA activity in mammalian cells. J. Med. Chem., 48(13), 4247-4253.

Scherer and Rossi (2004). Therapeutic applications of RNA interferences: recent advances in siRNA design. *Advances in Genetics*, 52, 1-21.

Schwarz et al. (2003). Asymmetry in the assembly of the RNAi enzyme complex. *Cell*, 115, 199-208.

Schwarz et al. (2006). Designing siRNA that distinguish between genes that differ by a single nucleotide. *PLoS Genetics*, 2(9), e140.

Sioud et al. (2004). Potential design rules and enzymatic synthesis of siRNAs. *Methods in Molec Biol.*, 252, 457-468.

Ui-Tei et al. (2006). Essential notes regarding the design of functional siRNAs for efficient mammalian RNAi. *J Biomed Biotechnol*, 2006, 65052.

Ui-Tei et al. (2008). DNA-modified siRNA-dependent gene silencing with reduced off-target effect is induced through a pathway parallel to that for siRNA-mediated RNA interference. Proceedings from Micro-NanoMechatronics and Human Science, 2008, 339-345.

Ui-Tei et al. (2008). Functional dissection of siRNA sequence by systematic DNA substitution: modified siRNA with a DNA seed arm is a powerful tool for mammalian gene silencing with significantly reduced off-target effect. *Nucleic Acids Research*, 36(7), 2136-2151.

Zamore et al. (2000). RNAi: Double-stranded RNA directs the ATP-dependent cleavage of mRNA at 21 to 23 nucleotide intervals. *Cell*, 101, 25-33.

Written Opinion of the International Searching Authority, mailed Mar. 22, 2011 in connection with PCT International Application No. PCT/US2010/058123, filed Nov. 25, 2010 (Publication No. WO 2011/066475, published Jun. 3, 2011).

International Search Report, mailed Mar. 22, 2011 in connection with PCT International Application No. PCT/US2010/58123, filed Nov. 25, 2010 (Publication No. WO 2011/066475, published Jun. 3, 2011).

Notification Concerning Transmittal of International Preliminary Report on Patentability (Chapter I of the Patent Cooperation Treaty), including an International Preliminary Report on Patentability and Written Opinion of the International Searching Authority, mailed Jun. 7, 2012 in connection with PCT International Application No. PCT/US2010/058123, filed Nov. 25, 2010.

Ui-Tei et al. (2004) Guidelines for the selection of highly effective siRNA sequences for mammalian and chick RNA interference. Nucleic Acids Research 32(3), 936-948.

Grimson et al. (2007) MicroRNA targeting specificity in mammals: Determinants beyond pairing. Molecular Cell, 27(1), 91-105.

Chalk et al. (2004) Improved and automated prediction of effective siRNA. Biochem Biophys Res Comm 319, 264-274.

Levenkova (2004) Gene specific siRNA selector. Bioinformatics, 20(3), 430-432.

De Paula (2007) Hydrophobization and bioconjugation for enhanced siRNA delivery and targeting. RNA, 13: 431-456.

Boutla (2001) Short 5'-phosphorylated double-stranded RNAs induce RNA interference in *Drosophila*, Current Biology, 11:1776-1780.

Schwarz (2002) Evidence that sIRNAs Function as Guides, Not Primers, in the *Drosophila* and Human RNAi Pathways. Molecular Cell, vol. 10, 537-548.

Bitko (2005) Inhibition of respiratory viruses by nasally administered siRNA. Nature Medicine, 11(1), 50-55.

(56) References Cited

OTHER PUBLICATIONS

Nov. 19, 2012 Office Action in connection with U.S. Appl. No. 13/511,111.
Feb. 19, 2013 Amendment in Response to Nov. 19, 2012 Office Action filed in connection with U.S. Appl. No. 13/511,111.
Apr. 5, 2013 Office Action in connection with U.S. Appl. No. 13/511,111.
Oct. 2, 2013 Amendment in Response to Apr. 5, 2013 Office Action filed in connection with U.S. Appl. No. 13/511,111.
Dec. 9, 2013 Final Office Action in connection with U.S. Appl. No. 13/511,111.
Jan. 27, 2014 Response to Dec. 9, 2013 Final Office Action filed in connection with U.S. Appl. No. 13/511,111.
Feb. 10, 2014 Advisory Action in connection with U.S. Appl. No. 13/511,111.
Feb. 27, 2014 Amendment in Response to Dec. 9, 2013 Final Office Action filed in connection with U.S. Appl. No. 13/511,111.
Mar. 26, 2014 Notice of Allowance issued in connection with U.S. Appl. No. 13/511,111.

1. Guide strand (AS): 5′ terminal nucleotide mismatch to target RNA

Target C. AS G > U, dU, rA, dA, rT, dT
Target G. AS C > U, dU, rA, dA, rT, dT
Target U. AS A > U, dU, dA, rT, dT Passenger strand (SEN): full match to AS

2. Guide strand (AS): 5′ terminal deoxyribonucleotide (dN¹) complementary to target RNA

```
                          SEQUENCE LISTING

<160> NUMBER OF SEQ ID NOS: 14

<210> SEQ ID NO 1
<211> LENGTH: 1492
<212> TYPE: RNA
<213> ORGANISM: HOMO_SAPIENS

<400> SEQUENCE: 1
cgggcgacag cagggccgcg gugcaguguc cgacccgaga guugcggccu gagucaccgg     60
ccccgcccuc cggagccgga cgcugcggga ggcccgggag cggcagugga accgacuccc    120
agaacuccgg acgugugcgg cgcagugagu cgcagccaug uuccugguua acucguucuu    180
gaagggcggc ggcggcggcg gcgggggagg cggggccug ggugggggcc ugggaaaugu    240
gcuuggaggc cugaucagcg gggccggggg cggcggcggc ggcggcggcg gcggcggcgg    300 uggugaggc ggcgguggcg guggaacggc caugcgcauc cuaggcggag ucaucagcgc    360
caucagcgag gcggcugcgc aguacaaccc ggagccccg ccccacgca cacauuacuc     420 caacauugag gccaacgaga gugaggaggu ccggcaguuc cggagacucu uugcccagcu    480
ggcuggagau gacauggagg ucagcgccac agaacucaug aacauucuca auaagguugu    540
gacacgacac ccugaucuga agacugaugg uuuuggcauu gacacauguc gcagcauggu    600
ggccgugaug gauagcgaca ccacaggcaa gcugggcuuu gaggaauuca aguacuugug    660
gaacaacauc aaaagguggc aggccauaua caaacaguuc gacacugacc gaucagggac    720
cauuugcagu agugaacucc caggugccuu ugaggcagca ggguccacc ugaaugagca    780 ucucuauaaac augaucaucc gacgcuacuc agaugaaagu gggaacaugg auuuugacaa    840
cuucaucagc ugcuugguca ggcuggacgc cauguuccgu gccuucaaau cucuugacaa    900
agauggcacu ggacaaaucc aggugaacau ccaggagugg cugcagcuga cuauguauuc    960
cugaacugga gccccagacc cgcccccuca cugccuugcu auaggaguca ccuggagccu   1020
cggucucucc cagggccgau ccugucugca gucacaucuu uggggccu gcugacccac    1080 aagcuuuugu ucucucagua cuuguacc agcuuccuca cauccagggc ccaauuugcc    1140
cugccuggag uuccccugg cucuaggaca cucuaacaag cucuguccac gggucucccc    1200
auucccacca ggcccugcac acaccacuc cguaaccucu ccccuguacc ugugccaagc    1260
cuagcacuug ugaugccucc augccccgag ggcccucucu caguucuggg aggaugacuc   1320
cagucccugc acgccuggcc acaccuuca cgguugcuac ccaggcggcc aagcuccaga    1380
ccgugccaga cccaggugcc ccagugccuu ugucuauauu cugcucccag ccugccaggc    1440
ccaggaggaa auaaacaugc cccaguugcu gaucucuaaa aaaaaaaaaa aa            1492
```

<210> SEQ ID NO 2
<211> LENGTH: 1489
<212> TYPE: RNA
<213> ORGANISM: HOMO_SAPIENS

<400> SEQUENCE: 2

```
cgggcgacag cagggccgcg gugcagoguc cgacccgaga guugcggccu gagucaccgg      60
ccccgcccuc cggagccgga cgcugcggga ggcccgggag cggcagugga accgacuccc     120
agaacuccgg acgugugcgg cgugagucgc agccauguuc cugguuaacu cguucuugaa     180
gggcggcggc ggcggcggcg ggggaggcgg gggccugggu gggggccugg gaaaugugcu     240
uggaggccug aucagcgggg ccggggggcgg cggcggcggc ggcggcggcg gcggcggugg     300
uggaggcggc ggugggcggug gaacggccau gcgcauccua ggcggaguca ucagcgccau     360
cagcgaggcg gcugcgcagu acaacccgga gccccgccc ccacgcacac auuacuccaa     420
cauugaggcc aacgagagug aggaggucccg gcaguccgg agacucuuug cccagcuggc     480
uggagaugac auggagguca gcgccacaga acucaugaac auucucaaua agguugugac     540
acgacacccu gaucugaaga cugauggguu uggcauugac acaugucgca gcaugguggc     600
cgugauggau agcgacacca caggcaagcu gggcuuugag gaauucaagu acuuguggaa     660
caacaucaaa aggugggcagg ccauauacaa acaguucgac acugaccgau caggggccau     720
uugcaguagu gaacucccag gugccuuuga ggcagcaggg uuccaccuga augagcaucu     780
cuauaacaug aucauccgac gcuacucaga ugaaaguggg aacauggauu uugcaacuu     840
caucagcugc uuggucaggc uggacgccau guuccgugcc uucaaaucuc uugacaaaga     900
uggcacugga caaauccagg ugaacaucca ggaguggcug cagcugacua uguauuccug     960
aacuggagcc ccagacccgc ccccucacug ccuugcuaua ggagucaccu ggagccucgg    1020
ucucucccag ggccgauccu gucucgaguc acaucuuugu ggggccugcu gacccacaag    1080
cuuuuguucu cucaguacuu guuacccagc uucucaacau ccagggccca auugcccug    1140
ccuggaguuc ccccuggcuc uaggacacuc uaacaagcuc uguccacggg ucucccauu    1200
cccaccaggc ccugcacaca cccacuccgu aaccucuccc cuguaccugu gccaagccua    1260
gcacuuguga ugccuccaug cccccgagggc ccucucucag uucugggagg augacuccag    1320
ucccugcacg cccuggcaca cccuucacgg uugcuaccca ggcggccaag cuccagaccg    1380
ugccagaccc aggugcccca gugccuuugu cuauauucug cucccagccu gccaggccca    1440
ggaggaaaua aacaugcccc agugcugau cucuaaaaaa aaaaaaaaa                 1489
```

<210> SEQ ID NO 3
<211> LENGTH: 1926
<212> TYPE: RNA
<213> ORGANISM: HOMO_SAPIENS

<400> SEQUENCE: 3

```
guggaugagc ugugagugcg cgcgcgugcg cggggccgcg accugugccg gcucgagccc      60
gcugggcacu cggaggcgcg cacgucguuc cccgcccucc cgccgccgcc cgcccucgcu     120
cucucgcgcu acccucccgc cgcccgcggu ccuccgucgg uucucucguu agccacggu     180
cuggucuuca gcuacccgcc uucgucuccg aguuugcgac ucgcggaccg gcguccccgg     240
cgcgaagagg cuggacucgg auucguugcc ugagcaaugg cugccauccg gaagaaacug     300
gugauuguug gugauggagc cuguggaaag acaugcuugc ucauagucuu cagcaaggac    360
```

| | |
|---|---|
| caguucccag agguguaugu gcccacagug uuugagaacu auguggcaga uaucgaggug | 420 |
| gauggaaagc agguagaguu ggcuuugugg gacacagcug ggcaggaaga uuaugaucgc | 480 |
| cugaggcccc ucuccuaccc agauaccgau guuauacuga uguguuuuuc caucgacagc | 540 |
| ccugauaguu uagaaaacau cccagaaaag uggaccccag aagucaagca uuucugcccc | 600 |
| aacgugccca ucauccuggu ugggaauaag aaggaucuuc ggaaugauga gcacacaagg | 660 |
| cgggagcuag ccaagaugaa gcaggagccg gugaaaccug aagaaggcag agauauggca | 720 |
| aacaggauug gcgcuuuugg guacauggag guucagcaa agaccaaaga uggagugaga | 780 |
| gagguuuuug aaauggcuac gagagcugcu cugcaagcua gacgugggaa gaaaaaaucu | 840 |
| gggugccuug ucuugugaaa ccuugcugca agcacagccc uuaugcgguu aauuuugaag | 900 |
| ugcuguuuau uaaucuuagu guaugauuac uggccuuuuu cauuuaucua uaauuuaccu | 960 |
| aagauuacaa aucagaaguc aucuugcuac caguauuuag aagccaacua ugauuauuaa | 1020 |
| cgauguccaa cccgucuggc ccaccagggu ccuuugaca cugcucuaac agcccuccuc | 1080 |
| ugcacuccca ccugacacac caggcgcuaa uucaaggaau uucuuaacuu cuugcuucu | 1140 |
| ucuagaaaga gaaacaguug guaacuuuug ugaauuaggc uguaacuacu uuauaacuaa | 1200 |
| cauguccugc cuauuaucug ucagcugcaa gguacucugg ugagcacca cuucagggcu | 1260 |
| uuacuccgua acaguuuug uggcauagc ucuggggugg gcaguuuuuu gaaaaugggc | 1320 |
| ucaaccagaa aagcccaagu ucaugcagcu gggcagagu uacaguucug gguuucaug | 1380 |
| uuaguuaccu uauaguuacu guguaauuag ugccacuuaa uguauguuac caaaaauaaa | 1440 |
| uauaucuacc ccagacuaga guagauauuu uuuguauaau uggauuuccu aauacuguca | 1500 |
| uccucaaaga aaguguauug guuuuuuaaa aagaaagug uauuuggaaa uaaagucaga | 1560 |
| uggaaaauuc auuuuuuaaa uucccguuuu gucacuuuuu cugauaaaag auggccauau | 1620 |
| uaccccuuuu cggcccaug uaucucagua ccccauggag cugggcuaag uaaauaggaa | 1680 |
| uugguuucac gccugaggca auuagacacu uggaagaug gcauaaccug ucucaccugg | 1740 |
| acuuaagcau cuggcucuaa uucacagugc ucuuuucucc ucacuguauc cagguucccu | 1800 |
| cccagaggag ccaccaguuc ucaugggugg cacucagucu cucuucucuc cagcugacua | 1860 |
| aacuuuuuuu cuguaccagu uaauuuuucc aacuacuaau agaauaaagg caguuuucua | 1920 |
| aaaaaa | 1926 |

<210> SEQ ID NO 4
<211> LENGTH: 3417
<212> TYPE: RNA
<213> ORGANISM: HOMO_SAPIENS

<400> SEQUENCE: 4

| | |
|---|---|
| cggaggcagc gagaaagcgc agccaggcgg cugcucggcg uucucucagg ugacugcucg | 60 |
| gaguucuccc aguguuuggu guugcaagca ggauccaaag gagaccuaua gugacuccca | 120 |
| ggagcucuua gugaccaagu gaaggauccu ggggggcuca uugugcccau ugcucuuuca | 180 |
| cugcuuucaa cugguaguug ugggguugaag cacuggacaa ugccacauac uuuguggaug | 240 |
| gugugggucu uggggucau caucagcccu ccaaggaag aauccuccaa ucaggcuucu | 300 |
| cugucuugug accgcaaugg uaucgcaag ggcagcucag gaucuuuaaa cuccauuccc | 360 |
| ucagggcuca cagaagcugu aaaaagccuu gaccugucca caacaggau caccuacauu | 420 |
| agcaacagug accuacagag gugugugaac cuccaggcuc uggucugac auccaaugga | 480 |
| auuaacacaa uagaggaaga uucuuuucu ucccugggca gucuugaaca uuuagacuua | 540 |

```
uccuauaauu acuuaucuaa uuuaucgucu uccugguuca agccccuuuc uucuuuaaca    600
uucuuaaacu uacugggaaa uccuuacaaa acccaggggg aaacaucucu uuuuucucau    660
cucacaaaau ugcaaauccu gagaguggga aauauggaca ccuucacuaa gauucaaaga    720
aaagauuuug cuggacuuac cuuccuugag gaacuugaga uugaugcuuc agaucuacag    780
agcuaugagc caaaaaguuu gaagucaauu cagaauguaa gucaucugau ccuucauaug    840
aagcagcaua uuuuacugcu ggagauuuuu guagauguua caaguccgu ggaauguuug     900 gaacugcgag auacugauuu ggacacuuuc cauuuuucag aacuauccac uggugaaaca    960
aauucauuga uuaaaaaguu uacauuuaga aaugugaaaa ucaccgauga aaguuuguuu   1020
cagguuauga aacuuuugaa ucagauuucu ggauuguuag aauuagaguu ugaugacugu   1080
acccuuaaug gaguugguaa uuuuagagca ucugauaaug acagaguuau agauccaggu   1140
aaagugaaaa cguuaacaau ccggaggcug cauauuccaa gguuuuacuu auuuuaugau   1200
cugagcacuu uauauucacu uacagaaaga guuaaaagaa ucacaguaga aaacaguaaa   1260
guuuuucugg uuccuuguuu acuuucacaa cauuuaaaau cauuagaaua cuuggaucuc   1320
agugaaaauu ugauggauga agaauacuug aaaaauucag ccugugagga ugccuggccc   1380
ucucuacaaa cuuuaauuuu aaggcaaaau cauuggcau cauggaaaa aaccggagag    1440 acuuugcuca cucugaaaaa cuugacuaac auugauauca guaagaauag uuucauucu    1500 augccugaaa cuugucagug gccagaaaag augaaauauu gaacuuauc cagcacacga    1560 auacacagug uaacaggcug cauucccaag acacuggaaa uuuuagaugu uagcaacaac   1620
aaucucaauu uauuuucuuu gaauuugccg caacucaaag aacuuuauau uuccagaaau   1680
aaguugauga cucuaccaga ugccuccccuc uuacccaugu uacuaguauu gaaaaucagu   1740
aggaaugcaa uaacuacguu uucuaaggag caacuugacu cauuucacac acugaagacu   1800
uuggaagcug guggcaauaa cuucauuugc uccugugaau uccucuccuu cacucaggag   1860
cagcaagcac uggccaaagu cuugauugau uggccagcaa auuaccugug ugacucucca   1920
ucccaugugc guggccagca gguucaggau guccgccucu cggugucgga augcacagg    1980 acagcacugg ugcuggcau gugcugugcu cguuccugc ugauccugcu cacgggggguc   2040 cugugccacc guuuccaugg ccuguggauu augaaaauga guggggccug gcuccaggcc   2100
aaaaggaagc ccaggaaagc ucccagcagg aacaucugcu augaugcauu uguucuuac    2160 agugagcggg augccuacug gguggagaac cuuaugggcc aggagcugga gaacuucaau   2220
ccccccuuca aguugugucu ucauaagcgg gacuucauuc cuggcaagug gaucauugac   2280
aauaucauug acuccauuga aaagagccac aaaacugucu uugucuuuc ugaaaacuuu    2340 gugaagagug aguggugcaa guaugaacug gacuucccc auuccgucu uuugaugag     2400 aacaaugaug cugccauucu cauucuucug gagcccauug agaaaaaagc cauuccccag   2460
cgcuucugca gcugcggaa gauaaugaac accaagaccu accuggagug gccauggac    2520 gaggcucagc gggaaggauu ugggguaaau cugagagcug cgauaaaguc cuagguuccc   2580
auauuuaaga ccagucuuug cuaguuggg aucuuuaugu cacuaguuau aguuaaguuc    2640
auucagacau aauuauauaa aaacuacgug gauguaccgu cauuugagga cuugcuuacu   2700
aaaacuacaa aacuucaaau uuugucuggg gugcuguuuu auaaacauau gccagauuua   2760
aaaauugguu uuugguuuuu cuuuuuucua ugagauaacc augaucauaa gucuauuacu   2820
gauaucugaa uauagucccu ugguauccaa gggaauuggu ugcaggaucc ucguggauau   2880
```

-continued

```
caaaauucau agaugaucaa gucccuuaua agaguggcau aguauuugca uauaaccugu    2940
guacauucuc cuguauacuu uaaaucaucu cuagauuacu uaugauaccc aaaucaaugu    3000
aaauacuaug uaaauaguug uacugucuuu uuauuuauau uauuauuguu auuuuuauu     3060 uucaaaauuu uuaaaacaua cuuuugaucc acaguugguu gacuucaugg augcagaacc    3120
cauggauaua gagggccaac uguaaucugu agcaacuggc uuaguucauu aggaaacagc    3180
acaaaugaac uuaagauucu caaugacugu gucauucuuu cuccugcua agagacuccu     3240 cuguggccac aaaaggcauu cucuguccua ccuagcuguc acuucucugu gcagcugauc    3300
ucaagagcaa caaggcaaag uauuuggggc acuccccaaa acuuguugcu auuccuagaa    3360
aaaagugcug uguauuuccu auuaaacuuu acaggaugag aaaaaaaaaa aaaaaaa      3417
```

<210> SEQ ID NO 5
<211> LENGTH: 19
<212> TYPE: RNA
<213> ORGANISM: artificial
<220> FEATURE:
<223> OTHER INFORMATION: Chemically synthesized

<400> SEQUENCE: 5
gagaugacau ggaggucag                                                 19

<210> SEQ ID NO 6
<211> LENGTH: 19
<212> TYPE: RNA
<213> ORGANISM: Artificial Sequence
<220> FEATURE:
<223> OTHER INFORMATION: Chemically synthesized

<400> SEQUENCE: 6
cugaccucca ugucaucuc                                                 19

<210> SEQ ID NO 7
<211> LENGTH: 19
<212> TYPE: RNA
<213> ORGANISM: artificial
<220> FEATURE:
<223> OTHER INFORMATION: Chemically synthesized

<400> SEQUENCE: 7
gaguggugca aguaugaac                                                 19

<210> SEQ ID NO 8
<211> LENGTH: 19
<212> TYPE: RNA
<213> ORGANISM: Artificial Sequence
<220> FEATURE:
<223> OTHER INFORMATION: Chemically synthesized

<400> SEQUENCE: 8
guucauacuu gcaccacuc                                                 19

<210> SEQ ID NO 9
<211> LENGTH: 19
<212> TYPE: RNA
<213> ORGANISM: artificial
<220> FEATURE:
<223> OTHER INFORMATION: Chemically synthesized

<400> SEQUENCE: 9
gguggagaac cuuaugguc                                                 19

```
<210> SEQ ID NO 10
<211> LENGTH: 19
<212> TYPE: RNA
<213> ORGANISM: Artificial Sequence
<220> FEATURE:
<223> OTHER INFORMATION: Chemically synthesized

<400> SEQUENCE: 10
gaccauaagg uucuccacc                                                19

<210> SEQ ID NO 11
<211> LENGTH: 19
<212> TYPE: RNA
<213> ORGANISM: artificial
<220> FEATURE:
<223> OTHER INFORMATION: Chemically synthesized

<400> SEQUENCE: 11
agauaaugaa caccaagac                                                19

<210> SEQ ID NO 12
<211> LENGTH: 19
<212> TYPE: RNA
<213> ORGANISM: Artificial Sequence
<220> FEATURE:
<223> OTHER INFORMATION: Chemically synthesized

<400> SEQUENCE: 12
gucuuggugu ucauuaucu                                                19

<210> SEQ ID NO 13
<211> LENGTH: 19
<212> TYPE: RNA
<213> ORGANISM: artificial
<220> FEATURE:
<223> OTHER INFORMATION: Chemically synthesized

<400> SEQUENCE: 13
gaucuucgga augaugaga                                                19

<210> SEQ ID NO 14
<211> LENGTH: 19
<212> TYPE: RNA
<213> ORGANISM: Artificial Sequence
<220> FEATURE:
<223> OTHER INFORMATION: Chemically synthesized

<400> SEQUENCE: 14
ucucaucauu ccgaagauc                                                19
```

SIRNA COMPOUNDS COMPRISING TERMINAL SUBSTITUTIONS

RELATED APPLICATIONS

This application is a divisional of U.S. Ser. No. 13/511,111, filed May 21, 2012, now allowed, which is a §371 national stage of PCT International Application No. PCT/US2010/058123, filed Nov. 25, 2010, which claims the benefit of U.S. Provisional Applications Nos. 61/264,668, filed Nov. 26, 2009; 61/295,721, filed Jan. 17, 2010; and 61/372,072, filed Aug. 9, 2010, the contents of each of which are hereby incorporated by reference in their entirety.

REFERENCE TO SEQUENCE LISTING

This application incorporates-by-reference nucleotide and/or amino acid sequences which are present in the file named "140804_2094_84023-Z_Sequence_Listing_AHC.txt," which is 13.1 kilobytes in size, and which was created Aug. 4, 2014 in the IBM-PC machine format, having an operating system compatibility with MS-Windows, which is contained in the text file filed Aug. 4, 2014 as part of this application.

FIELD OF THE INVENTION

The present invention relates to modified siRNA compounds, pharmaceutical compositions comprising same and methods of use thereof for the inhibition of gene expression. The compounds and compositions exhibit beneficial properties including knock down activity of target genes and are useful in the treatment of subjects suffering from diseases or conditions and or symptoms associated with such diseases or conditions or at risk of contracting diseases or conditions in which gene expression has adverse. consequences.

BACKGROUND OF THE INVENTION

PCT Patent Publication Nos. WO 2008/104978 and WO 2009/044392 to the assignee of the present invention and hereby incorporated by reference in their entirety, disclose novel siRNA structures.

There remains a need for active and effective siRNA therapeutic agents which exhibit enhanced knock down activity, increased stability and or reduced off target effects.

SUMMARY OF THE INVENTION

The double stranded RNA (dsRNA) compounds disclosed herein possess structures and modifications which may, for example increase activity, increase stability, reduce immunogenicity, enhance loading into the RISC complex, and or minimize toxicity; the novel modifications of the siRNAs are beneficially applied to double stranded RNA useful in preventing or attenuating target gene expression.

Provided herein are double stranded (duplex) oligonucleotide compounds useful for the down regulation of gene expression. The present disclosure is based in part on the unexpected observation that a double stranded nucleic acid molecule comprising a sense strand and a complementary antisense strand and having a mismatch between the 5' terminal nucleotide of the antisense strand and the nucleotide of the target RNA show potent activity in down regulating target genes. In preferred embodiments the dsRNA comprises an adenosine, deoxyadenosine, uridine, deoxyuridine, ribothymidine or thymidine substituted at position 1 (5' terminus) of the antisense strand rather in place of a cytidine or guanine.

According to one aspect provided are modified double stranded nucleic acid molecules having structure (A) set forth below:

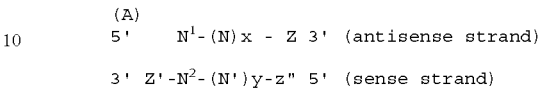

wherein each of $N^2$, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y has complementarity to the sequence of (N)x and (N)x has complementarity to a consecutive sequence in a target RNA;

wherein $N^1$ is covalently bound to (N)x and is mismatched to the target RNA or is a complementary DNA moiety to the target RNA;

wherein $N^1$ is a moiety selected from the group consisting of natural or modified uridine, deoxyribouridine, ribothymidine, deoxyribothymidine, adenosine or deoxyadenosine;

wherein z" may be present or absent, but if present is a capping moiety covalently attached at the 5' terminus of $N^2$—(N')y; and wherein each of Z and Z' is independently present or absent, but if present is independently 1-5 consecutive nucleotides, consecutive non-nucleotide moieties or a combination thereof covalently attached at the 3' terminus of the strand in which it is present.

In some embodiments the sequence of (N')y is fully complementary to the sequence of (N)x. In various embodiments sequence of $N^2$ (N')y is complementary to the sequence of $N^1$—(N)x. In some embodiments (N)x comprises an antisense that is fully complementary to about 17 to about 39 consecutive nucleotides in a target RNA. In other embodiments (N)x comprises an antisense that is substantially complementary to about 17 to about 39 consecutive nucleotides in a target RNA.

In some embodiments $N^1$ and $N^2$ form a Watson-Crick base pair. In some embodiments $N^1$ and $N^2$ form a non-Watson-Crick base pair. In some embodiments a base pair is formed between a ribonucleotide and a deoxyribonucleotide.

In some embodiments x=y=18, x=y=19 or x=y=20. In preferred embodiments x=y=18.

In some embodiments $N^1$ is covalently bound to (N)x and is mismatched to the target RNA. In various embodiments $N^1$ is covalently bound to (N)x and is a DNA moiety complementary to the target RNA.

In some embodiments a uridine in position 1 of the antisense strand is substituted with an $N^1$ selected from adenosine, deoxyadenosine, deoxyuridine, ribothymidine or deoxythymidine. In various embodiments $N^1$ selected from adenosine, deoxyadenosine or deoxyuridine.

In some embodiments guanosine in position 1 of the antisense strand is substituted with an $N^1$ selected from adenosine, deoxyadenosine, uridine, deoxyuridine, ribothymidine or deoxythymidine. In various embodiments $N^1$ is selected from adenosine, deoxyadenosine, uridine or deoxyuridine.

In some embodiments cytidine in position 1 of the antisense strand is substituted with an $N^1$ selected from adenosine, deoxyadenosine, uridine, deoxyuridine, ribothymidine or deoxythymidine. In various embodiments $N^1$ is selected from adenosine, deoxyadenosine, uridine or deoxyuridine.

In some embodiments adenosine in position 1 of the antisense strand is substituted with an $N^1$ selected from deoxyadenosine, deoxyuridine, ribothymidine or deoxythymidine. In various embodiments $N^1$ selected from deoxyadenosine or deoxyuridine.

In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

In some embodiments the double stranded nucleic acid molecule is a siRNA, siNA or a miRNA.

The following table provides examples of N1 and corresponding N2.

| Target nucleotide | 5' terminal nucleotide of AS with Full match to target | N1 (5' terminal position of AS) | N2 (3' terminal position of SEN) |
|---|---|---|---|
| A | U | rA, dA | rU, dU, rT, dT |
| A | U | dU, rT, dT | rA, dA |
| C | G | rA, dA | rU, dU, rT, dT |
| C | G | rU, dU, rT, dT | rA, dA |
| G | C | rA, dA | rU, dU, rT dT |
| G | C | rU, dU, rT, dT | rA, dA |
| U | A | dA | rU, dU, rT, dT |
| U | A | dU, rT, dT | rA, dA |

In some embodiments of Structure (A), $N^1$ comprises uridine or adenosine. In certain embodiments of structure (A), $N^2$ comprises a 2'OMe sugar modified ribonucleotide. In some embodiments of Structure (A). $N^1$ comprises 2'OMe sugar-modified ribouridine and $N^2$ comprises adenosine or modified adenosine. In some embodiments of Structure (A), $N^1$ comprises adenosine and $N^2$ comprises a ribouridine or modified ribouridine.

In some embodiments Z and Z' are absent. In other embodiments one of Z or Z' is present.

In some embodiments each of N and N' is an unmodified ribonucleotide. In some embodiments at least one of N or N' comprises a chemically modified ribonucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' comprises a 2'OMe sugar-modified ribonucleotide.

In some embodiments the sequence of (N')y is fully complementary to the sequence of (N)x. In other embodiments the sequence of (N')y is substantially complementary to the sequence of (N)x.

In some embodiments (N)x comprises an antisense sequence that is fully complementary to about 17 to about 39 consecutive nucleotides in a target mRNA. In other embodiments (N)x comprises an antisense that is substantially complementary to about 17 to about 39 consecutive nucleotides in a target mRNA. In some embodiments x–y=18.

According to certain preferred embodiments siRNA compounds comprising one or more modified nucleotide, wherein the modified nucleotide possesses a modification in the sugar moiety, in the base moiety or in the internucleotide linkage moiety are provided.

Structure (A) motif is useful with any oligonucleotide pair (sense and antisense strands) to a mammalian or non-mammalian gene. In some embodiments the mammalian gene is a human gene.

In some embodiments a modified siRNA compound having structure (A) exhibits beneficial properties including enhanced activity (e.g. reduced IC50, increased knock down, reduced residual mRNA) when compared to a control compound, i.e. an siRNA compound wherein the antisense oligonucleotide is fully complementary (including 5' terminal nucleotide base paired e.g. A-U, U-A, C-G, G-C) to a nucleotide sequence in a target mRNA. In some embodiments the activity is enhanced by at least 5%, by at least 10%, by at least 20%, by at least 25% or more when compared to a control compound.

In another aspect the present invention provides a method of generating a double stranded RNA molecule consisting of a sense strand and an antisense strand comprising the steps of a) selecting a consecutive 17 to 25 nucleotide sequence in a target RNA and synthesizing an antisense strand comprising complementarity to the consecutive 17 to 25 nucleotide sequence of the target mRNA wherein the 5' terminal nucleotide of the antisense strand is substituted with uridine, modified uridine, ribothymidine, deoxyribothymidine, adenosine, modified adenosine, deoxyadenosine or modified deoxyadenosine, with the proviso that a rG:rU wobble is not generated between the 5' terminal nucleotide of the antisense strand and the 3' terminal nucleotide of the target mRNA;

b) synthesizing a sense strand of 17 to 25 nucleotides having complementarity to the antisense strand, wherein the 3' terminal nucleotide of the sense strand forms a Watson Crick base pair with the 5' terminal nucleotide of the guide strand; and c) annealing the antisense and sense strands; thereby generating a double stranded RNA molecule.

According to one aspect, the present invention provides a method of generating a double stranded RNA molecule consisting of a sense strand and an antisense strand exhibiting enhanced RNAi activity when compared to an unmodified a double stranded RNA molecule comprising the steps of a) selecting a consecutive 17 to 25 nucleotide sequence in a target mRNA and synthesizing a sense strand comprising the consecutive 17 to 25 nucleotide sequence of the target mRNA wherein the 3' terminal nucleotide is substituted with adenosine, modified adenosine, deoxyadenosine or modified deoxyadenosine;

b) synthesizing an antisense strand of 17 to 25 nucleotides having complementarity to the sense strand wherein the 5' terminal nucleotide comprises ribouridine, modified ribouridine, deoxyribouridine or modified deoxyribouridine and base pairs with the 3' terminal nucleotide of the passenger strand;

c) annealing the sense strand to the antisense strand;

thereby generating a double stranded RNA molecule having enhanced RNAi activity.

In some embodiments the modified double stranded RNA molecule exhibits enhanced RNAi activity when compared to an unmodified siRNA duplex, i.e. a duplex having full match to the target mRNA.

According to another aspect, the present invention provides a method of generating a modified a double stranded RNA molecule consisting of a sense strand and antisense strand exhibiting enhanced RNAi activity when compared to an unmodified a double stranded RNA molecule comprising the steps of a) selecting a consecutive 17 to 25 nucleotide sequence in a target mRNA and synthesizing a sense strand comprising the consecutive 17 to 25 nucleotide sequence of the target mRNA wherein the 3' terminal nucleotide is substituted with adenosine, modified adenosine, deoxyadenosine or modified deoxyadenosine;

b) synthesizing an antisense strand of 17 to 25 nucleotides having complementarity to the sense strand wherein the 5' terminal nucleotide comprises ribouridine, modified ribouridine, deoxyribouridine or modified deoxyribouridine and base pairs with the 3' terminal nucleotide of the sense strand;

c) annealing the sense strand to the antisense strand;

thereby generating a double stranded RNA molecule having enhanced RNAi activity.

In some embodiments step a) includes selecting a consecutive 17 to 25 nucleotide, or 17, 18, 19, 20, 21, 22, 23, 24 or 25 nucleotide sequence in a target RNA in a target cell wherein the 3' terminal nucleotide is other than adenosine.

In another aspect provided is a pharmaceutical composition comprising a compound according to Structure (A), in an amount effective to inhibit mammalian or non-mammalian gene expression; and a pharmaceutically acceptable carrier. In some embodiments the mammalian gene is a human gene. In some embodiments the non-mammalian gene is involved in a mammalian disease, preferably human disease.

Further provided are methods for treating or preventing the incidence or seventy of a disease or condition and/or for reducing the risk or severity of a disease or condition in a subject in need thereof wherein the disease or condition and/or a symptom and/or risk associated therewith is associated with expression of a mammalian or a non-mammalian gene. In a preferred embodiment the subject is a human subject.

In some embodiments the disease or condition is selected from the group hearing loss, acute renal failure (ARF), Delayed Graft Function (DGF) after kidney transplantation, glaucoma, ocular ischemic conditions including anterior ischemic optic neuropathy, age-related macular degeneration (AMD), Ischemic Optic Neuropathy (ION), dry eye syndrome, acute respiratory distress syndrome (ARDS) and other acute lung and respiratory injuries, chronic obstructive pulmonary disease (COPD), primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, organ transplantation including lung, liver, heart, pancreas, and kidney transplantation, nephro- and neurotoxicity, spinal cord injury, brain injury, neurodegenerative disease or condition, pressure sores, oral mucositis fibrotic conditions including liver fibrosis, lung fibrosis; and cancer. Such methods involve administering to a mammal in need of such treatment a prophylactically or therapeutically effective amount of one or more such compounds, which inhibit or reduce expression or activity of at least one such gene.

The compounds, methods, materials, and examples that will now be described are illustrative only and are not intended to be limiting; materials and methods similar or equivalent to those described herein can be used in practice or testing of the invention.

Other features and advantages of the invention will be apparent from the following detailed description, and from the claims.

DETAILED DESCRIPTION OF THE INVENTION

Figure 1:
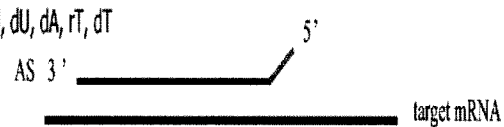
FIG. 1 is a diagram of the dsRNA molecules as provided herein. In one embodiment, the 5' terminal G or C nucleotide of the antisense strand is substituted with U, dU, rA, dA, rT, dT; or the 5' terminal U nucleotide of the antisense strand is substituted with dU, rA, dA, rT, dT; or the 5' terminal A nucleotide of the antisense strand is substituted with U, dU, dA, rT, dT. In one embodiment the 5' terminal nucleotide of the antisense strand is mismatched to the target mRNA. In another embodiment the 5' terminal nucleotide of the antisense strand is a deoxyribonucleotide complementary to the target mRNA.
Figure 1:
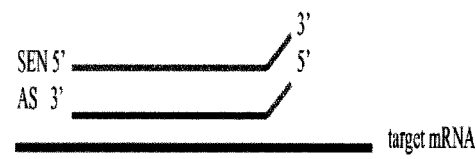
Figure 1:
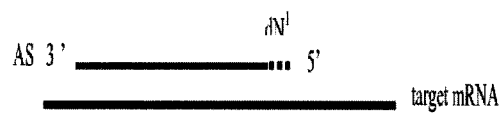

The present invention relates generally to oligonucleotide compounds which down-regulate expression of various genes, particularly to small interfering RNAs (siRNA), specifically to modified siRNA compounds and to the use of these modified siRNA compounds in preparation of pharmaceutical compositions and in treatment of a subject suffering from various medical conditions.

The compounds and compositions exhibit beneficial properties including potent knock down activity of target genes and are useful in the treatment of subjects suffering from diseases or conditions and or symptoms associated with such diseases or conditions or at risk of contracting diseases or conditions in which gene expression has adverse consequences.

Accordingly, in certain aspects modified siRNA compounds and pharmaceutical compositions comprising same useful in down regulating gene expression are provided.

In another aspect, the present invention provides a method of treating a subject suffering from or susceptible to a microvascular disorder, eye disease or disorder, hearing impairment (including hearing loss), a respiratory (including pulmonary) disorder, neurodegenerative disease or disorder, spinal cord injury, brain injury angiogenesis- and apoptosis-related conditions comprising administering to the subject a pharmaceutical composition comprising at least one small interfering RNA of the invention that targets a mammalian or non-mammalian gene, in an amount sufficient to down-regulate the expression of the gene.

In certain embodiments, the subject compounds are useful in inhibiting expression of a target gene for treatment of inter alia, respiratory disorders, microvascular disorders or eye disorders. Particular diseases and conditions to be treated are ARDS; COPD; ALI; Emphysema; Diabetic Neuropathy, nephropathy and retinopathy; DME and other diabetic conditions; Glaucoma; AMD; BMT retinopathy; ischemic conditions including stroke; OIS; neurodegenerative disorders such as Parkinson's, Alzheimer's, ALS; kidney disorders: ARF, DGF, transplant rejection; hearing disorders; spinal cord injuries; oral mucositis; cancer, dry eye syndrome and pressure sores.

Definitions

For convenience certain terms employed in the specification, examples and claims are described herein.

It is to be noted that, as used herein, the singular forms "a", "an" and "the" include plural forms unless the content clearly dictates otherwise. Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein refers to a siRNA inhibitor. A "siRNA inhibitor" is a compound that is capable of reducing the expression of a gene or the activity of the product of such gene to an extent sufficient to achieve a desired biological or physiological effect. The term "siRNA inhibitor" as used herein refers to one or more of a siRNA, shRNA, siNA, synthetic shRNA; miRNA. Inhibition may also be referred to as down-regulation or, for RNAi, silencing.

The term "inhibit" as used herein refers to reducing the expression of a gone or the activity of the product of such gene to an extent sufficient to achieve a desired biological or physiological effect. Inhibition is either complete or partial As used herein, the term "inhibition" of a target gene means inhibition of the gene expression (transcription or translation) or polypeptide activity of the product of a target gene. "Gene product" as used herein, refers to a product of a gene such as an RNA transcript or a polypeptide. The terms "RNA transcript", "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this disclosure, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides, nucleotide analogues, modified nucleotide analogues, unconventional and abasic moieties and combinations thereof.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

"Nucleotide" is meant to encompass deoxyribonucleotides and ribonucleotides, which may be natural or synthetic and modified or unmodified. Nucleotides include known nucleotide analogues, which are synthetic, naturally occurring, and non-naturally occurring. Examples of such analogs include, without limitation, phosphorothioates, phosphoramidites, methyl phosphonates, chiral-methyl phosphonates, 2'-O-methyl ribonucleotides, and peptide-nucleic acids (PNAs). Modifications include changes to the sugar moiety, the base moiety and or the linkages between ribonucleotides in the oligoribonucleotide. As used herein, the term "ribonucleotide" encompasses natural and synthetic, unmodified and modified ribonucleotides and ribonucleotide analogues which are synthetic, naturally occurring, and non-naturally occurring. Modifications include changes to the sugar moiety, to the base moiety and/or to the linkages between ribonucleotides in the oligonucleotide.

The nucleotides are selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halouracil, 5-halocytosine, 6-azacytosine and 6-az thymine, pseudouracil, deoxypseudouracil, 4-thiouracil, ribo-2-thiouridine, ribo-4-thiouridine, 8-haloadenine, 8-aminoadenine, 8-thioladenine, 8-thiolalkyl adenines, 8-hydroxyl adenine and other 8-substituted adenines, 8-haloguanines, 8-aminoguanine, 8-thiolguanine, 8-thioalkyl-guanines 8-hydroxylguanine and other substituted guanines, other aza and deaza adenines, other aza and deaza guanines, 5-methylribouridine, 5-trifluoromethyl uracil, 5-methylribocytosine, and 5-trifluorocytosine. In some embodiments one or more nucleotides in an oligomer is substituted with inosine.

In some embodiments the siRNA compound further comprises at least one modified ribonucleotide selected from the group consisting of a ribonucleotide having a sugar modification, a base modification or an internucleotide linkage modification and may contain DNA, and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), or nucleotides with a 6 carbon sugar.

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenosine 3' phosphonoacetate, deoxyribocytidine 3' phosphonoacetate, deoxyriboguanosine 3' phosphonoacetate, deoxyribothymidine 3' phosphonoacetate).

Bridged nucleic acids include LNA (2'-O, 4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

All analogs of, or modifications to, a nucleotide/oligonucleotide are employed with the present invention, provided that said analog or modification does not substantially adversely affect the properties, e.g. function, of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy (e.g. methoxy), alkyl, amino, fluoro, chloro, bromo, CN, CF, imidazole, carboxylate, thioate, C1 to C10 lower alkyl, substituted lower alkyl, alkaryl or aralkyl, $OCF_3$, OCN, O-, S-, or N-alkyl; O-, S-, or N-alkenyl; $SOCH_3$;

SO$_2$CH$_3$; ONO$_2$; NO$_2$, N$_3$; heterocycloalkyl; heterocycloalkaryl; aminoalkylamino; polyalkylamino or substituted silyl, as, among others, described in European patents EP 0 586 520 B1 or EP 0 618 925 B1.

In one embodiment the modified siRNA compound comprises at least one ribonucleotide comprising a 2' modification on the sugar moiety ("2' sugar modification"). In certain embodiments the siRNA compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me riboU, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments the non-base pairing nucleotide analog is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have enhanced stability in vivo and in vitro. Other modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

In some embodiments the compounds of the present invention are synthesized with one or more inverted nucleotides, for example inverted thymidine or inverted adenosine (see, for example, Takei, et al., 2002, JBC 277(26):23800-06).

Other modifications include 3' terminal modifications also known as capping moieties. Such terminal modifications are selected from a nucleotide, a modified nucleotide, a lipid, a peptide, a sugar and inverted abasic moiety. Such modifications are incorporated, for example at the 3' terminus of the sense and/or antisense strands.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thionucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA.

A "hydrocarbon moiety or derivative thereof" refers to straight chain or branched alkyl moieties and moieties per se or further comprising a functional group including alcohols, phosphodiester, phosphorothioate, phosphonoacetate and also includes amines, carboxylic acids, esters, amides aldehydes. "Hydrocarbon moiety" and "alkyl moiety" are used interchangeably.

"Terminal functional group" includes halogen, alcohol, amine, carboxylic, ester, amide, aldehyde, ketone, ether groups.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including locked nucleic acids (LNA) and ethylene bridged nucleic acids (ENA).

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate.

Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouridine-3'-phosposphate (mirror dU).

According to one aspect the present invention provides inhibitory modified siRNA compounds comprising unmodified ribonucleotides, modified ribonucleotides and/or unconventional moieties. In some embodiments the modified siRNA compound comprises at least one modified nucleotide selected from the group consisting of a sugar modification, a base modification and an internucleotide linkage modification and may contain modified nucleotides such as LNA (locked nucleic acid) including ENA (ethylene-bridged nucleic acid; PNA (peptide nucleic acid); arabinoside; PACE (phosphonoacetate and derivatives thereof), or nucleotides with a six-carbon sugar or an unconventional moiety selected from an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond. In some embodiments a modified ribonucleotide is a 2'OMe sugar modified ribonucleotide.

In some embodiments the siRNA is blunt ended at the 3' terminus of the compound, i.e. the siRNA is blunt ended on the end defined by the 3'-terminus of the sense or passenger strand and the 5'-terminus of antisense or guide strand.

In other embodiments at least one of the two strands has a 3' overhang of at least one nucleotide at the 3'-terminus; the overhang comprises at least one deoxyribonucleotide. At least one of the strands optionally comprises an overhang of at least one nucleotide at the 3'-terminus. The overhang consists of from about 1 to about 5 nucleotides.

In various embodiments the overhangs are independently selected from a nucleotide, a non-nucleotide and a combination thereof. In certain embodiments, each overhang, if present, is independently selected from a ribonucleotide, deoxyribonucleotide, abasic deoxyribose moiety, abasic deoxyribose moiety, C3-amino-Pi, C4-amino-Pi, C5-amino-Pi, C6-amino-Pi, a mirror nucleotide.

In some embodiments each of Z and/or Z' independently includes a C(2, C3, C4, C5 or C6 alkyl moiety, optionally a C3 [propane, —(CH2)₃—] moiety or a derivative thereof including propanol (C3-OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In a specific embodiment x=y=19 and Z comprises C3-C3. In some embodiments the C3-C3 overhang is covalently attached to the 3' terminus of (N)x or (N')y via a covalent linkage, for example a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH.

In various embodiments the alkyl moiety comprises an alkyl derivative including a C3 alkyl, C4 alkyl, C5 alkyl or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof.

The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate.

In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof.

In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)₃, (propyl phosphate)₂-propanol, (propyl phosphate)₂-propyl phosphorothioate. Any propane or propanol conjugated moiety can be included in Z or Z'.

The structures of exemplary 3' terminal non-nucleotide moieties are as follows:

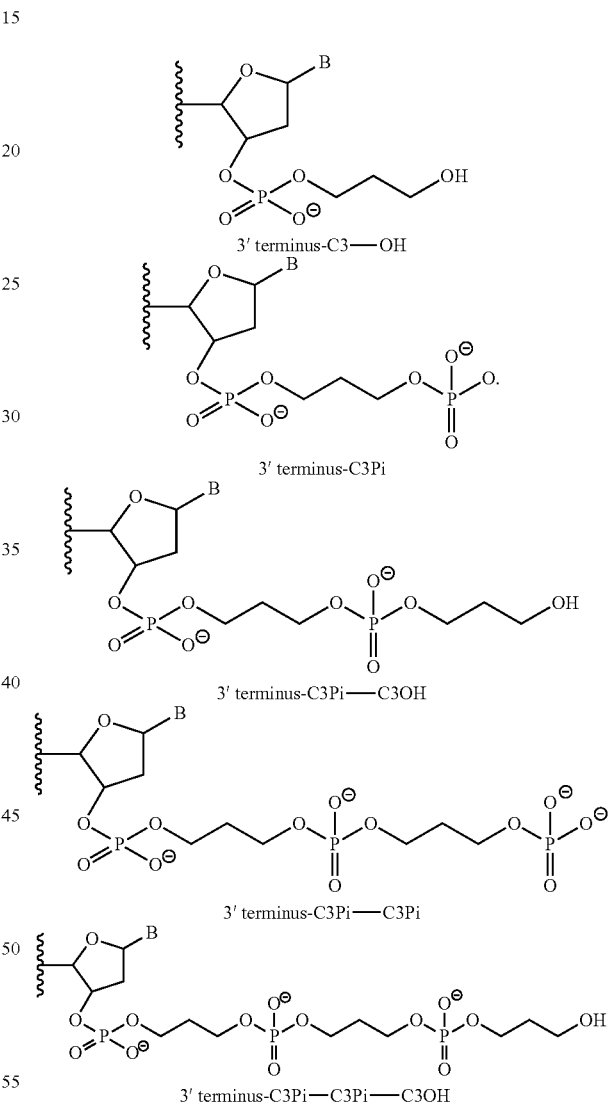

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3Pi-rAb or C3Pi-dAb.

The length of RNA duplex is from about 18 to about 40 ribonucleotides, preferably 19 to 23 ribonucleotides. In some embodiments the length of each strand (oligomer) is independently selected from the group consisting of about 18 to about 40 bases, preferably 18 to 23 bases and more preferably 19, 20 or 21 ribonucleotides.

In some embodiments, the complementarity between the antisense strand of the modified siRNA compound and the target nucleic acid is perfect. In other embodiments, the antisense strand of the modified siRNA compound and the target nucleic acid are substantially complementary, i.e. having one, two or up to three mismatches between said antisense strand and the target nucleic acid.

In certain embodiments the complementarity between the antisense strand and the sense strand of the modified siRNA compound of present invention is perfect. In some embodiments, the strands are substantially complementary, i.e. having one, two or up to three mismatches between said antisense strand and said sense strand.

The siRNAs compounds of the present invention possess a terminal moiety covalently bound at the 5'-terminus of the antisense strand which is mismatched to a nucleotide in a target mRNA. In various embodiments the moiety at the 5'-terminus of the antisense strand is selected form the group consisting of ribouridine, deoxyribouridine, modified ribouridine, modified deoxyribouridine, pseudouracil, deoxypseudouracil, deoxyribothymidine, modified deoxyribothymidine, ribocytosine, modified ribocytosine, deoxyribocytosine, modified deoxyribocytosine, 5-methylribocytosine, modified 5-methylribocytosine, 5-methylribouridine, modified 5-methylribouridine, ribo-2-thiouridine, ribo-4-thiouridine, abasic ribose moiety and abasic deoxyribose moiety.

In some embodiments the modified siRNA compounds of the invention exhibit enhanced activity, when compared to an siRNA compound wherein the antisense strand including the 5'-terminal nucleotide is fully complementary to a consecutive sequence in a target mRNA.

The siRNA structures of the present invention are beneficially applied to double stranded RNA useful in inhibiting or attenuating mammalian and non-mammalian gene expression.

siRNA Oligonucleotides

In one aspect the present invention provides a compound having structure (A) set forth below:

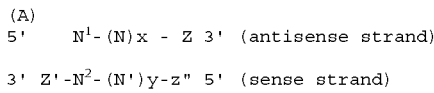

wherein each of $N^2$, N and N' is an unmodified or modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein the sequence of (N')y has complementarity to the sequence of (N)x and (N)x has complementarity to a consecutive sequence in a target RNA;
wherein $N^1$ is covalently bound to (N)x and is mismatched to the target RNA or is a DNA moiety complementary to the target RNA;
wherein $N^1$ is a moiety selected from the group consisting of natural or modified uridine, deoxyribouridine, ribothymidine, deoxyribothymidine, adenosine or deoxyadenosine;
wherein z" may be present or absent, but if present is a capping moiety covalently attached at the 5' terminus of $N^2$—(N')y; and wherein each of Z and Z' is independently present or absent, but if present is independently 1-5 consecutive nucleotides, consecutive non-nucleotide moieties or a combination thereof covalently attached at the 3' terminus of the strand in which it is present.

In some embodiments $N^1$ is covalently bound to (N)x and is mismatched to the target RNA.

In some embodiments $N^1$ is covalently bound to (N)x and is a DNA moiety complementary to the target RNA.

In some embodiments $N^1$ and $N^2$ together form a Watson-Crick base pair. In other embodiments $N^1$ and $N^2$ together form a non-Watson-Crick base pair.

In some embodiments x=y=18. In other embodiments x=y=19. In yet other embodiments x=y=20. In preferred embodiments x=y=18.

In some embodiments $N^1$ is a modified ribocytosine or a modified ribouridine. In certain embodiments of $N^1$ modified ribocytosine or modified ribouridine is selected from the group comprising 5-methylribocytosine, modified 5-methylribocytosine, 5-methylribouridine, ribo-2-thiouridine and ribo-4-thiouridine.

In certain embodiments $N^1$ is selected from the group consisting of ribocytosine, modified ribocytosine, deoxyribocytosine, modified deoxyribocytosine, 5-methylribocytosine and modified 5-methylribocytosine. In other embodiments $N^1$ is selected from the group consisting of ribouridine, deoxyribouridine, modified ribouridine, modified deoxyribouridine, pseudouracil, deoxypseudouracil, 5-methylribouridine, ribo-2-thiouridine and ribo 4-thiouridine. In some embodiments $N^1$ is deoxyribothymidine or modified deoxyribothymidine.

In some embodiments $N^2$ is a modified ribonucleotide or an unmodified ribonucleotide. In certain embodiments $N^2$ is selected from the group comprising riboguanine, modified riboguanine, deoxyguanine, modified deoxyguanine, ribouridine, modified ribouridine, deoxyribouridine, modified deoxyribouridine, adenosine, modified adenosine, deoxyadenosine, modified deoxyadenosine, ribocytosine, modified ribocytosine, deoxyribocytosine and modified deoxyribocytosine.

In some embodiments N2 is selected from the group consisting of riboguanine, modified riboguanine, deoxyguanine, ribouridine, deoxyribouridine, adenosine, deoxyadenosine, ribocytosine and deoxyribocytosine. In other embodiments N2 is selected from the group consisting of ribouridine, modified ribouridine, deoxyribouridine, modified deoxyribouridine, adenosine, modified adenosine, deoxyadenosine, modified deoxyadenosine, ribocytosine, modified ribocytosine, deoxyribocytosine and modified deoxyribocytosine. In yet other embodiments N2 is selected from the group consisting of ribouridine, modified ribouridine, deoxyribouridine, modified deoxyribouridine, adenosine, modified adenosine, deoxyadenosine, modified deoxyadenosine, ribocytosine, modified ribocytosine, deoxyribocytosine and modified deoxyribocytosine.

In certain embodiments $N^1$ is selected from the group consisting of ribocytosine, modified ribocytosine, deoxyribocytosine, modified deoxyribocytosine, 5-methylribocytosine and modified 5-methylribocytosine and $N^2$ is selected from the group consisting of riboguanine, modified riboguanine, deoxyguanine, ribouridine, deoxyribouridine, adenosine, deoxyadenosine, ribocytosine and deoxyribocytosine.

In some embodiments $N^1$ is selected from the group consisting of ribouridine, deoxyribouridine, modified ribouridine, modified deoxyribouridine, pseudouracil, deoxypseudouracil, 5-methylribouridine, ribo-2-thiouridine and ribo 4-thiouridine and $N^2$ is selected from the group consisting of ribouridine, modified ribouridine, deoxyribouridine, modified deoxyribouridine, adenosine, modified adenosine, deoxyadenosine, modified deoxyadenosine, ribocytosine, modified ribocytosine, deoxyribocytosine and modified deoxyribocytosine.

In certain embodiments $N^1$ is deoxyribothymidine or modified deoxyribothymidine and $N^2$ is selected from the group consisting of ribouridine, modified ribouridine, deoxyribouridine, modified deoxyribouridine, adenosine, modified adenosine, deoxyadenosine, modified deoxyadenosine, ribocytosine, modified ribocytosine, deoxyribocytosine and modified deoxyribocytosine.

In some embodiments of Structure (A), $N^1$ comprises 2'OMe sugar modified ribouridine or 2'OMe sugar modified ribocytosine. In certain embodiments of structure (A), $N^2$ comprises a 2'OMe sugar modified ribonucleotide.

In some embodiments Z and Z' are absent. In other embodiments one of Z or Z' is present.

In various embodiments Z and Z' are independently selected from a nucleotide, a non-nucleotide and a combination thereof. In certain embodiments, each of Z and Z', if present, is independently selected from a ribonucleotide, deoxyribonucleotide, abasic deoxyribose moiety, abasic deoxyribose moiety, C3-amino-Pi, C4-amino-Pi, C5-amino-Pi, C6-amino-Pi, a mirror nucleotide. In some embodiments Z is present. In other embodiments Z' is present. In additional embodiments both Z and Z' are present. In some embodiments Z and Z' are present and are identical. In further embodiments Z and Z' are present and are different. In some embodiments Z and Z' are independently 1, 2, 3, 4 or 5 non-nucleotide moieties or a combination of 2, 3, 4, or 5 non-nucleotide moieties and nucleotides. In some embodiments each of Z and or Z' comprises 2 non-nucleotide moieties covalently linked to the 3' terminus of the siRNA strand via a phosphodiester bond. In some embodiments Z and Z' are present and each one independently comprises one or more alkyl moieties and or derivative thereof. In some embodiments, $N^2$ comprises riboadenosine and $N^1$ comprises uridine (ribouridine).

A non-nucleotide moiety is selected from the group consisting of an abasic moiety, an inverted abasic moiety, an alkyl moiety or derivative thereof, and an inorganic phosphate. In some embodiments a non-nucleotide moiety is an alkyl moiety or derivative thereof. In some embodiments the alkyl moiety comprises a terminal functional group including alcohol, a terminal amine, a terminal phosphate or a terminal phosphorothioate moiety.

In some embodiments Z is present and comprises one or more non-nucleotide moieties selected from the group consisting of an abasic moiety, an inverted abasic moiety, hydrocarbon moiety or derivative thereof, and an inorganic phosphate. In some embodiments Z is present and comprises one or more alkyl moieties and or derivative thereof.

In additional embodiments Z' is present and comprises one or more non-nucleotide moieties selected from the group consisting of an abasic moiety, an inverted abasic moiety, a hydrocarbon moiety, and an inorganic phosphate. In some embodiments Z' is present and comprises one or more alkyl moieties and or derivative thereof.

In additional embodiments x=y=18 and either Z or Z' is present and independently comprises two non-nucleotide moieties.

In additional embodiments x=y=18 and Z and Z' are present and each independently comprises two non-nucleotide moieties.

In some embodiments each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb. Each moiety is covalently conjugated an adjacent moiety via a covalent bond, preferably a phospho-based bond. In some embodiments the phospho-based bond is a phosphorothioate, a phosphonoacetate or a phosphodiester bond.

In some embodiments each of Z and/or Z' independently includes an alkyl moiety, optionally propane [(CH2)$_3$] moiety or a derivative thereof including propanol (C3-OH) and phospho derivative of propanediol ("C3-3'Pi"). In some embodiments each of Z and/or Z' includes two hydrocarbon moieties and in some examples is C3-C3. Each C3 is covalently conjugated an adjacent C3 via a covalent bond, preferably a phospho-based bond. In some embodiments the phospho-based bond is a phosphorothioate, a phosphonoacetate or a phosphodiester bond.

In a specific embodiment x=y=18 and Z comprises C3Pi-C3OH or C3Pi-C3Pi. In a specific embodiment x=y=18 and Z comprises C3Pi-C3OH or C3Pi-C3Pi. In some embodiments the C3-C3 overhang is covalently attached to the 3' terminus of (N)x or (N')y via covalent linkage, for example a phosphodiester linkage. In some embodiments the linkage between a first C3 and a second C3 is a phosphodiester linkage.

In various embodiments the alkyl moiety is a C3 alkyl to C6 alkyl moiety comprising a terminal hydroxyl, a terminal amino, terminal phosphate group. In some embodiments the alkyl moiety is a C3 alkyl moiety. In some embodiments the C3 alkyl moiety comprises propanol, propylphosphate, propylphosphorothioate or a combination thereof.

The C3 alkyl moiety is covalently linked to the 3' terminus of (N')y and or the 3' terminus of (N)x via a phosphodiester bond. In some embodiments the alkyl moiety comprises propanol, propyl phosphate or propyl phosphorothioate.

In some embodiments each of Z and Z' is independently selected from propanol, propyl phosphate, propyl phosphorothioate, combinations thereof or multiples thereof.

In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)$_3$, (propyl phosphate)$_2$-propanol, (propyl phosphate)$_2$-propyl phosphorothioate. Any propane or propanol conjugated moiety can be included in Z or Z'.

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3-rAb or C3-dAb.

In preferred embodiments x=y=18, Z' is absent, Z is present and comprises two alkyl moieties covalently linked to each other via a phosphodiester bond, $N^2$ comprises riboadenosine and $N^1$ comprises uridine.

In some embodiments N and N' comprise an unmodified nucleotide. In some embodiments at least one of N or N' comprises a chemically modified ribonucleotide or an unconventional moiety. In some embodiments the unconventional moiety is selected from the group consisting of a mirror nucleotide, an abasic ribose moiety, an abasic deoxyribose moiety, a deoxyribonucleotide, a modified deoxyribonucleotide, a mirror nucleotide, a non-base pairing nucleotide analog, a bridged nucleic acid and a nucleotide joined to an adjacent nucleotide by a 2'-5' internucleotide phosphate bond. In some embodiments the unconventional moiety is a mirror nucleotide, preferably an L-DNA moiety. In some embodiments at least one of N or N' is modified at one or more of the sugar, the base or linker. In certain embodiments at least one of N or N' comprises a 2'OMe sugar modified ribonucleotide.

In certain embodiments (N)x and (N')y are fully complementary. In other embodiments (N)x and (N')y are substantially complementary. In certain embodiments (N)x is fully complementary to a target sequence. In other embodiments (N)x is substantially complementary to a target sequence. According to certain preferred embodiments the present invention provides a modified siRNA compound comprising one or more modified nucleotide, wherein the modified nucleotide possesses a modification in the sugar moiety, in the base moiety or in the internucleotide linkage moiety.

In certain embodiments of the compound according to Structure (A) alternating ribonucleotides in each of $(N)_x$ and $(N')_y$ are 2'-OMe sugar-modified ribonucleotides. In some embodiments of Structure (A) in (N)x the nucleotides are unmodified or (N)x comprises alternating 2'OMe sugar modified ribonucleotides and unmodified ribonucleotides; and the ribonucleotide located at the middle position of $N^1$—(N)x being modified or unmodified preferably unmodified; wherein (N')y comprises unmodified ribonucleotides further comprising one modified nucleotide at a terminal or penultimate position.

In particular embodiments, x=y=18, $N^1$ comprises 2'OMe sugar modified ribonucleotide, (N)x comprises 2'OMe sugar modified ribonucleotides and the ribonucleotide located at the middle of $N^1$—(N)x is unmodified. In some embodiments at least one nucleotide at either or both the 5' and 3' termini of (N')y are joined by a 2'-5' phosphodiester bond. In some embodiments $N^1$ is joined to the 5' terminus of (N)x by a 2'-5' phosphodiester bond. In some embodiments at least one nucleotides at either or both the 5' and 3' termini of (N')x are joined by a 2'-5' phosphodiester bond. In some embodiments $N^2$ is joined to the 3' terminus of (N)y by a 2'-5' phosphodiester bond. In certain embodiments x=y=18; in (N)x the nucleotides alternate between modified ribonucleotides and unmodified ribonucleotides, each modified ribonucleotide is a 2'OMe sugar modified ribonucleotide and the ribonucleotide located at the middle of $N^1$—(N)x being unmodified; $N^2$ is joined to the 3' terminus of (N)y by a 2'-5' phosphodiester bond and at least two nucleotides at the 3' terminus of (N')y are joined by two 2'-5' phosphodiester bonds. In other preferred embodiments, x=y=18; in (N)x the nucleotides alternate between modified ribonucleotides and unmodified ribonucleotides, each modified ribonucleotide is a 2'-OMe sugar modified ribonucleotide and the ribonucleotide located at the middle of $N^1$—(N)x being unmodified; and at least three consecutive nucleotides at the 5' terminus of (N')y are joined by three 2'-5' phosphodiester bonds. In a further embodiment, the nucleotide located in the middle position of $N^2$—(N)y, i.e. nucleotide at position 10, is a 2'OMe sugar modified ribonucleotide. In another preferred embodiment, in (N)x the nucleotides alternate between 2'-OMe sugar modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-OMe sugar modification.

In certain preferred embodiments, x=y=18 and in (N')y the nucleotide in at least one position comprises a mirror nucleotide, a deoxyribonucleotide and a nucleotide joined to an adjacent nucleotide by a 2'-5' internucleotide bond.

In certain embodiments, x=y=18 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 17. In other embodiments (N')y comprises L-DNA at positions 16 and 17. In certain embodiments (N')y comprises L-DNA nucleotides at positions 1 and at one or both of positions 16 and 17.

In yet other embodiments (N')y comprises a DNA at position 14 and L-DNA at one or both of positions 16 and 17. In that structure, position 1 may further comprise an L-DNA or an abasic unconventional moiety.

In other embodiments wherein x=y=20 the modifications for (N')y discussed above instead of being on positions 14, 15, 16, 17 are on positions 17, 18, 19, 20. For example, the modifications at one or both of positions 16 and 17 are on one or both of positions 18 or 19 for the 20-mer. All modifications in the 18-mer are similarly adjusted for the 20- and 22-mer.

According to various embodiments in $N^2$—(N')y, $N^2$ is joined to the 3' terminus of (N)y by a 2'-5' phosphodiester bond and in (N')y 1, 2, 3, 4, 5, 6, 7, 8, 9, 10, 11, 12 or 13 consecutive ribonucleotides at the 3' terminus are linked by 2'-5' internucleotide linkages. In one embodiment, $N^2$ is joined to the 3' terminus of (N)y by a 2'-5' phosphodiester bond and three consecutive nucleotides at the 3' terminus of (N')y are joined by three 2'-5' phosphodiester bonds, wherein one or more of the 2'-5' nucleotides which form the 2'-5' phosphodiester bonds further comprises a 3'-OMe sugar modification. In some embodiments $N^2$ comprises a 2'-OMe sugar modification. In further embodiments the 3' terminal nucleotide of (N')y comprises a 2'-OMe sugar modification. In certain embodiments x=y=18 and in (N')y two or more consecutive nucleotides at positions 14, 15, 16, 17 and 18 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 16 and 17 in (N')y are joined by a 2'-5' internucleotide bond. In other embodiments the nucleotides at positions 15-16, 16-17, or 15-17 in (N')y are joined by a 2'-5' internucleotide bond.

In certain embodiments (N')y comprises an L-DNA at position 2 and 2'-5' internucleotide bonds at positions 15-16, 16-17, or 15-17.

In one embodiment the 3' terminal nucleotide or two or three consecutive nucleotides at the 3' terminus of (N')y are L-deoxyribonucleotides.

In other embodiments in $N^2$—(N')y, $N^2$ is a 2' sugar modified nucleotide and in (N')y (N')y 1, 2, 3, 4, 5, 6, 7, 8, 9, 10, 11, 12 or 13 consecutive ribonucleotides at either terminus or 1 to 7 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In one series of embodiments, three, four or five consecutive nucleotides at the 5' terminus of (N')y comprise the 2'-OMe modification. In another embodiment, $N^2$ and two consecutive nucleotides at the 3' terminus of (N')y comprise the 2'-OMe modification.

In some embodiments in (N')y 1, 2, 3, 4, 5, 6, 7, 8, 9, 10, 11, 12 or 13 consecutive ribonucleotides at either or 1 to 7 modified nucleotides at each of the 5' and 3' termini are independently bicyclic nucleotides. In various embodiments the bicyclic nucleotide is a locked nucleic acid (LNA) or a species of LNA, e.g. 2'-O, 4'-C-ethylene-bridged nucleic acid (ENA) is a species of LNA.

In various embodiments (N')y comprises modified nucleotides at the 5' terminus or at both the 3' and 5' termini.

In some embodiments at least two nucleotides at the 5' of (N')y are joined by P-ethoxy backbone modifications. In some embodiments $N^2$ at the 3' of (N')y is joined by P-ethoxy backbone modifications. In certain embodiments x=y=18 and wherein in (N)x the nucleotides alternate between modified ribonucleotides and unmodified ribonucleotides, each modified ribonucleotide being a 2'OMe sugar modified ribonucleotide and the ribonucleotide located at the middle position of $N^1$—(N)x being unmodified; N1 being a 2'OMe sugar modified ribonucleotide and three consecutive nucleotides at the 3' terminus are joined by two P-ethoxy backbone modifications or four consecutive nucleotides at the 5' terminus of (N')y are joined by three P-ethoxy backbone modifications. In a further embodiment, $N^2$ at the 3' of (N')y is joined by P-ethoxy backbone modification.

In some embodiments in (N')y 1, 2, 3, 4, 5, 6 or 7, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one embodiment, four consecutive nucleotides at the 5' terminus of (N')y are joined by three 2'-5' phosphodiester bonds and two or three consecutive nucleotides at the 3' terminus of (N')y are joined by two 2'-5' phosphodiester bonds. In a further embodiment $N^2$ at the 3' of (N')y is joined at the 3' terminus of (N')y by a 2'-5' phosphodiester bond. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and two consecutive nucleotides at the 3' terminus of (N')y are joined by two 2'-5' phosphodiester bonds. In (N)x the nucleotides alternate between 2'OMe sugar modified ribonucleotides and unmodified ribonucleotides, and the ribonucleotide located at the middle of $N^1$—(N)x is unmodified.

In various embodiments, $N^2$ is joined at the 3' terminus of (N')y by a 2'-5' phosphodiester bond and two or three consecutive nucleotides at the 3' terminus of (N')x are joined by one or two 2'-5' phosphodiester bonds. In some embodiments, $N^2$ is joined at the 3' terminus of (N')y by a 2'-5' phosphodiester bond and two or three consecutive nucleotides at the 3' terminus of (N')x are joined by one or two 2'-5' phosphodiester bonds and one or two or three consecutive nucleotides at the 3' terminus comprise 3'-OMe sugar modification. In a further embodiment $N^2$ comprise 3'-OMe sugar modification.

In another embodiment the present invention provides a compound wherein x=y=18 and wherein in (N)x the nucleotides alternate between modified ribonucleotides and unmodified ribonucleotides, each modified ribonucleotide being a 2'OMe sugar modified ribonucleotide and the ribonucleotide located at the middle of $N^1$—(N)x being unmodified; two nucleotides at the 3' terminus of (N')y are joined by two 2'-5' phosphodiester bonds and three nucleotides at the 5' terminus of (N')y are LNA such as ENA. In a further embodiment $N^2$ is joined at the 3' terminus of (N')y by a 2'-5' phosphodiester bond.

In another embodiment five consecutive nucleotides at the 5' terminus of (N')y comprise the 2'OMe sugar modification and two consecutive nucleotides at the 3' terminus of (N')y are L-DNA.

In yet another embodiment, the present invention provides a compound wherein x=y=18 wherein (N)x consists of unmodified ribonucleotides; two consecutive nucleotides at the 3' terminus of (N')y are joined by a 2'-5' phosphodiester bonds and three consecutive nucleotides at the 5' terminus of (N')y are LNA such as ENA. In a further embodiment $N^2$ is joined at the 3' terminus of (N')y by a 2'-5' phosphodiester bond.

According to other embodiments in (N')y the 5' or 3' terminal nucleotide, or 2, 3, 4, 5 or 6 consecutive nucleotides at either termini or 1 to 4 nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides.

In some embodiments, neither strand of the modified siRNA compounds of the invention is phosphorylated at the 3' and 5' termini. In other embodiments the sense and antisense strands are phosphorylated at the 3' termini. In yet another embodiment, the antisense strand is phosphorylated at the terminal 5' termini position using cleavable or non-cleavable phosphate groups. In yet another embodiment, either or both antisense and sense strands are phosphorylated at the 3' termini position using cleavable or non-cleavable phosphate groups.

Structure (A) is useful with any oligonucleotide pair (sense and antisense strands) to a mammalian or non-mammalian gene. In some embodiments the mammalian gene is a human gene. Examples of oligonucleotide sequence pairs are provided in PCT Patent Publication Nos. WO 2006/023544, WO 2007/084684, WO 2008/050329, WO 2007/141796, WO 2009/044392, WO 2008/106102, WO 2008/152636, WO 2009/001359, WO/2009/090639 assigned to the assignee of the present invention and incorporated herein by reference in their entirety.

Unless otherwise indicated, in preferred embodiments of the structures discussed herein the covalent bond between each consecutive N and N' is a phosphodiester bond. Unless otherwise indicated, in preferred embodiments of the structures discussed herein the covalent bond between $N^1$ and (N)x and between $N^2$ and (N')y is a phosphodiester bond. In some embodiments at least one of the covalent bond is a phosphorothioate bond.

For all of the structures above, in some embodiments the oligonucleotide sequence of (N)x is fully complementary to the oligonucleotide sequence of (N')y. In other embodiments the antisense and sense strands are substantially complementary. In certain embodiments (N)x is fully complementary to a mammalian mRNA or microbial RNA or viral RNA. In other embodiments (N)x is substantially complementary to a mammalian mRNA or microbial RNA or viral RNA.

In some embodiments a modified siRNA compound having structure (A) exhibits beneficial properties including at least enhanced activity when compared to an siRNA compound wherein $N^1$ is complementary to a nucleotide in a target mRNA.

The present invention further provides a pharmaceutical composition comprising a compound of the present invention according to Structure (A), in an amount effective to inhibit mammalian or non-mammalian gene expression, and a pharmaceutically acceptable carrier, and use thereof for treatment of any one of the diseases and disorders disclosed herein. In some embodiments the mammalian gene is a human gene. In some embodiments the non-mammalian gene is involved in a mammalian disease, preferably human disease.

The present invention further relates to methods for treating or preventing the incidence or severity of any one of the diseases or conditions disclosed herein or for reducing the risk or severity of a disease or a condition disclosed herein in a subject in need thereof, wherein the disease or condition and/or a symptom or risk associated therewith is associated with expression of a mammalian or a non-mammalian gene. In a preferred embodiment the subject is a human subject.

siRNA Synthesis

Using public and proprietary algorithms the sense and antisense sequences of potential siRNAs are generated and $N^1$ and/or $N^2$ of the siRNAs are substituted to generate the modified siRNA compounds according to Structure (A).

siRNA molecules according to the above specifications are prepared essentially as described herein. The modified siRNA compounds of the present invention are synthesized by any of the methods that are well known in the art for synthesis of ribonucleic (or deoxyribonucleic) oligonucleotides. Synthesis is commonly performed in a commercially available synthesizer (available, inter alia, from Applied Biosystems). Oligonucleotide synthesis is described for example in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Ann. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, e.g. the procedures described in Usman at al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

In some embodiments the oligonucleotides of the present invention are synthesized separately and joined together post-synthetically, for example, by ligation (Moore at al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the modified siRNA compounds of the present invention, two or more such sequences can be synthesized and linked together for use in the present invention.

The siRNAs compounds of the present invention possess a terminal moiety covalently bound at the 5'-terminus of the antisense strand which is mismatched to a nucleotide in a target mRNA. In various embodiments the moiety at the 5'-terminus of the antisense strand is selected from the group consisting of ribouridine, deoxyribouridine, modified ribouridine, modified deoxyribouridine, pseudouracil, deoxypseudouracil, deoxyribothymidine, modified deoxyribothymidine, ribocytosine, modified ribocytosine, deoxyribocytosine, modified deoxyribocytosine, 5-methylribocytosine, modified 5-methylribocytosine, 5-methylribouridine, ribo-2-thiouridine, ribo-4-thiouridine, abasic ribose moiety and abasic deoxyribose moiety and the moiety at the 3'-terminus of the sense strand is selected from a ribonucleotide or a modified ribonucleotide or an unconventional moiety. The siRNA structures of the present invention are beneficially applied to double stranded RNA useful in inhibiting or attenuating mammalian and non-mammalian gene expression.

Pharmaceutical Compositions

While it is possible for the compounds of the present invention to be administered as the raw chemical, it is preferable to present them as a pharmaceutical composition. Accordingly the present invention provides a pharmaceutical composition comprising one or more of the modified siRNA compounds of the invention; and a pharmaceutically acceptable carrier. In some embodiments the pharmaceutical composition comprises two or more modified siRNA compounds of the invention.

The invention further provides a pharmaceutical composition comprising at least one compound of the invention covalently or non-covalently bound to one or more compounds of the invention in an amount effective to inhibit a target gene; and a pharmaceutically acceptable carrier. In some embodiments the modified siRNA compounds are processed intracellularly by endogenous cellular complexes to produce one or more oligoribonucleotides of the invention.

The invention further provides a pharmaceutical composition comprising a pharmaceutically acceptable carrier and one or more of the modified siRNA compounds of the invention in an amount effective to down-regulate expression in a cell in a mammal of a target gene, the compound comprising a sequence which is substantially complementary to the sequence of a target mRNA.

In some embodiments, the modified siRNA compounds according to the present invention are the main active component in a pharmaceutical composition. In other embodiments the modified siRNA compounds according to the present invention are one of the active components of a pharmaceutical composition containing two or more siRNAs, said pharmaceutical composition further being comprised of one or more siRNA compounds which target one or more target genes.

The present invention also provides for a process of preparing a pharmaceutical composition, which comprises:
providing one or more double stranded modified siRNA compound of the invention; and
admixing said compound with a pharmaceutically acceptable carrier.

In a preferred embodiment, the modified siRNA compound used in the preparation of a pharmaceutical composition is admixed with a carrier in a pharmaceutically effective dose. In some embodiments the modified siRNA compound of the present invention is conjugated to a steroid or to a lipid or to another suitable molecule e.g. to cholesterol.

RNA Interference

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing a siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., Genes Dev., 2001, 15(2):188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818):363-6; Lee et al., Nature, 2003, 425(6956): 415-9). The RISC protein complex recognizes these fragments and complementary mRNA. The whole process is culminated by endonuclease cleavage of target mRNA (McManus & Sharp, Nature Rev Genet, 2002, 3(10):737-47; Paddison & Hannon, Curr Opin Mol Ther. 2003, 5(3):217-24). (For additional information on these terms and proposed mechanisms, see for example Bernstein et al., RNA 2001, 7(11):1509-21; Nishikura, Cell 2001, 107(4):415-8 and PCT publication WO 01/36646).

The selection and synthesis of siRNA corresponding to known genes has been widely reported; see for example Ui-Tei et al., J Biomed Biotechnol. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., Nuc. Acid Res. 2004, 32(3):936-48. For examples of the use of, and production of, modified siRNA see Braasch et al., Biochem., 2003, 42(26):7967-75; Chiu et al., RNA, 2003, 9(9):1034-48; PCT publications WO 2004/015107 (Atugen); WO 02/44321 (Tuschl et al), and U.S. Pat. Nos. 5,898,031 and 6,107,094.

siRNA and RNA Interference

RNA interference (RNAi) is a phenomenon involving double-stranded (ds) RNA-dependent gene specific post-transcriptional silencing. Initial attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later, it was discovered that synthetic duplexes of 21 nucleotide RNAs could mediate gene specific RNAi in mammalian cells, without stimulating the generic antiviral defense mechanisms (see Elbashir et al. Nature 2001, 411: 494-498 and Caplen et al. PNAS USA 2001, 98:9742-9747). As a result, small interfering RNAs (siRNAs) have become powerful tools in attempting to understand gene function.

RNA interference (RNAi) in mammals is mediated by small interfering RNAs (siRNAs) (Fire et al, Nature 1998, 391:806) or microRNAs (miRNAs) (Ambros, Nature 2004, 431(7006):350-355; Bartel, Cell 2004, 116(2): 281-97). The corresponding process in plants is commonly referred to as specific post-transcriptional gene silencing (PTGS) or RNA silencing and is also referred to as quelling in fungi.

A siRNA is a double-stranded RNA or modified RNA molecule which down-regulates or silences (prevents) the expression of a gene/mRNA of its endogenous (cellular) counterpart. The mechanism of RNA interference is detailed infra.

Several studies have revealed that siRNA therapeutic agents are effective in vivo in both mammals and in humans. Bitko et al., have shown that specific siRNA molecules directed against the respiratory syncytial virus (RSV) nucleocapsid N gene are effective in treating mica when administered intranasally (Nat. Med. 2005, 11(1):50-55). Recent reviews discussing siRNA therapeutics are available (Barik, et al., J. Mol. Med 2005, 83:764-773; Dallas and Vlassov, Med. Sci. Monitor 2006, 12(4):RA67-74; Chakraborty, Current Drug Targets 2007, 8(3):469-82; Dykxhoorn et al., Gene Therapy 2006. 13:541-552).

Mucke (IDrugs 2007 10(1):37-41) presents a review of current therapeutics, including siRNA to various targets, for the treatment of ocular diseases, for example age related macular degeneration (AMD) and glaucoma.

siRNA Structures

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol Biol.; 2004, 252:457-69; Levenkova at al., Bioinform. 2004, 20(3):430-2; Ui-Tai at al., NAR. 2004, 32(3):936-48; De Paula et al., RNA 2007, 13:431-56).

For examples of the use of, and production of, modified siRNA see, for example, Braasch et al., Biochem. 2003, 42(26):7967-75; Chiu et al., RNA, 2003, 9(9):1034-48: PCT publications WO 2004/015107 (atugen AG) and WO 02/44321 (Tuschl et al). U.S. Pat. Nos. 5,898,031 and 6,107,094, describe chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz at al., Mol. Cell, 2002, 10:537-48). Amarzguioui et al., (NAR, 2003, 31(2):589-95) showed that siRNA activity depended on the positioning of the 2'-O-methyl modifications. Holen et at (NAR. 2003, 31(9): 2401-07) report that an siRNA having small numbers of 2'-O-methyl modified nucleosides gave good activity compared to wild type but that the activity decreased as the numbers of 2'-O-methyl modified nucleosides was increased. Chiu and Rana (RNA. 2003, 9:1034-48) describe that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the present invention offer an advantage in that they are stable and active and are useful in the preparation of pharmaceutical compositions for treatment of various diseases.

PCT Patent Publication Nos. WO 2008/104978 and WO 2009/044392 to the assignee of the present invention and hereby incorporated by reference in their entirety, disclose novel siRNA structures.

PCT Publication No. WO 2008/050329 and U.S. Ser. No. 11/978,089 to the assignee of the present invention relate to inhibitors of pro-apoptotic genes, and are incorporated by reference in their entirety.

PCT Patent Publication Nos. WO 2004/111191 and WO 2005/001043 relate to methods for enhancing RNAi.

The invention provides a method of down-regulating the expression of target gene by at least 20%, 30%, 40% or 50% as compared to a control, comprising contacting an mRNA transcript of the target gene with one or more of the compounds of the invention.

Additionally the invention provides a method of down-regulating the expression of target gene in a mammal by at least 20%, 30%, 40% or 50% as compared to a control, comprising administering one or more of the compounds of the invention to the mammal. In a preferred embodiment of the invention the mammal is a human.

In various embodiments a double stranded nucleic acid molecule of Structure (A) is down-regulating the expression of a target gene, whereby the down-regulation of the expression of a target gene is selected from the group comprising down-regulation of gene function (which is examined, e.g. by an enzymatic assay or a binding assay with a known interactor of the native gene/polypeptide, inter alia), down-regulation of polypeptide product of the gene (which is examined, e.g. by Western blotting, ELISA or immuno-precipitation, inter alia) and down-regulation of mRNA expression of the gene (which is examined, e.g. by Northern blotting, quantitative RT-PCR, in-situ hybridisation or microarray hybridisation, inter alia).

Delivery

The modified siRNA compound of the invention is administered as the compound per se (i.e. as naked siRNA) or as pharmaceutically acceptable salt and is administered alone or as an active ingredient in combination with one or more pharmaceutically acceptable carrier, solvent, diluent, excipient, adjuvant and vehicle. In some embodiments, the siRNA molecules of the present invention are delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Pharmaceutically acceptable carriers, solvents, diluents, excipients, adjuvants and vehicles as well as implant carriers generally refer to inert, non-toxic solid or liquid fillers, diluents or encapsulating material not reacting with the active modified siRNA compounds of the invention and they include liposomes and microspheres. For example, the siRNA compounds of the invention may be formulated with polyethylenimine (PEI), with PEI derivatives, e.g. oleic and stearic acid modified derivatives of branched PEI, with chitosan or with poly(lactic-co-glycolic acid) (PLGA). Formulating the compositions in e.g. liposomes, micro- or nano-spheres and nanoparticles, may enhance stability and benefit absorption.

Additionally, the compositions may include an artificial oxygen carrier, such as perfluorocarbons (PFCs) e.g. perfluorooctyl bromide (perflubron).

Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many such implants, delivery systems, and modules are well known to those skilled in the art. In one specific embodiment of this invention topical and transdermal formulations are selected.

Accordingly, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed (see, for example, Shen et al FEBS Let. 539: 111-114 (2003), Xia et al., Nat. Biotech. 20: 1006-1010 (2002), Reich et al., Mol. Vision 9: 210-216 (2003), Sorensen et al., J. Mol. Biol. 327: 761-766 (2003), Lewis et. al., Nat. Gen. 32: 107-108 (2002) and Simconi et al., NAR 31, 11: 2717-2724 (2003)). siRNA has recently been successfully used for inhibition of gene expression in primates; (for details see for example, Tolentino et al., Retina 2004. 24(1):132-138).

Additional formulations for improved delivery of the compounds of the present invention can include non-formulated compounds, compounds covalently bound to cholesterol, and compounds bound to targeting antibodies (Song et al., Antibody mediated in vivo delivery of small interfering RNAs via cell-surface receptors, Nat Biotechnol. 2005. 23(6):709-17). Cholesterol-conjugated siRNAs (and other steroid and lipid conjugated siRNAs) can been used for delivery (see for example Soutschek et al Nature. 2004. 432:173-177; and Lorenz et al. Bioorg. Med. Chem. Lett. 2004. 14:4975-4977).

The naked siRNA or the pharmaceutical compositions comprising the chemically modified siRNA of the present invention are administered and dosed in accordance with good medical practice, taking into account the clinical condition of the individual patient, the disease to be treated, the site and method of administration, scheduling of administration, patient age, sex, body weight and other factors known to medical practitioners.

A "therapeutically affective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The siRNA of the invention can be administered in a single dose or in multiple doses.

In general, the active dose of compound for humans is in the range of from 1 ng/kg to about 20-100 mg/kg body weight per day, preferably about 0.01 mg to about 2-10 mg/kg body weight per day, in a regimen of a single dose or a one dose per day or twice or three or more times per day for a period of 1-4 weeks or longer.

The modified siRNA compounds of the present invention can be administered by any of the conventional routes of administration. The modified siRNA compounds are administered orally, subcutaneously or parenterally including intravenous, intraarterial, intramuscular, intraperitoneally, intraocular, ocular, otic, transtympanic and intranasal administration, intratracheal instillation and intratracheal inhalation, as well as infusion techniques. Implants of the compounds are also useful.

Liquid forms are prepared for invasive administration, e.g. injection or for topical or local or non-invasive administration. The term injection includes subcutaneous, transdermal, intravenous, intramuscular, intrathecal, intraocular, transtympanic and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration.

In some embodiments the compounds of the present invention are formulated for non-invasive administration. In some embodiments the compounds of the present invention are formulated as eardrops for topical administration to the ear. In some embodiments the compounds of the present invention are formulated as eye drops for topical administration to the surface of the eye. Further information on administration of the compounds of the present invention can be found in Tolentino et al., Retina 2004. 24:132-138; and Reich et al., Molecular Vision, 2003. 9:210-216. In addition, in certain embodiments the compositions for use in the treatments of the present invention are formed as aerosols, for example for intranasal administration. In certain embodiments the compositions for use in the treatments of the present invention are formed as nasal drops, for example for intranasal instillation.

The therapeutic compositions of the present invention are preferably administered into the lung by inhalation of an aerosol containing these compositions/compounds, or by intranasal or intratracheal instillation of said compositions. For further information on pulmonary delivery of pharmaceutical compositions see Weiss et al., Human Gene Therapy 1999. 10:2287-2293; Densmore et al., Molecular therapy 1999. 1:180-188; Gautam et al., Molecular Therapy 2001. 3:551-556; and Shahiwala & Misra, AAPS PharmSciTech 2004. 24;6(3):E482-6. Additionally, respiratory formulations for siRNA are described in U.S. Patent Application Publication No. 2004/0063654. Respiratory formulations for siRNA are described in US Patent Application Publication No. 2004/0063654.

In certain embodiments, oral compositions (such as tablets, suspensions, solutions) may be effective for local delivery to the oral cavity such as oral composition suitable for mouthwash for the treatment of oral mucositis.

In a particular embodiment, the modified siRNA compounds of the invention are formulated for intravenous administration for delivery to the kidney for the treatment of kidney disorders, e.g. acute renal failure (ARF), delayed graft function (DGF) and diabetic retinopathy. It is noted that the delivery of the modified siRNA compounds according to the present invention to the target cells in the kidney proximal tubules is particularly effective in the treatment of ARF and DGF.

Delivery of compounds into the brain is accomplished by several methods such as, inter alia, neurosurgical implants, blood-brain barrier disruption, lipid mediated transport, carrier mediated influx or efflux, plasma protein-mediated transport, receptor-mediated transcytosis, absorptive-mediated transcytosis, neuropeptide transport at the blood-brain barrier, and genetically engineering "Trojan horses" for drug targeting. The above methods are performed, for example, as described in "*Brain Drug Targeting: the future of brain drug development*", W. M. Pardridge, Cambridge University Press, Cambridge, UK (2001).

In addition, in certain embodiments the compositions for use in the treatments of the present invention are formed as aerosols, for example for intranasal administration.

Intranasal delivery for the treatment of CNS diseases has been attained with acetylcholinesterase inhibitors such as galantamine and various salts and derivatives of galantamine, for example as described in US Patent Application Publication No. 2006003989 and PCT Applications Publication Nos. WO 2004/002402 and WO 2005/102275. Intranasal delivery of nucleic acids for the treatment of CNS diseases, for example by intranasal instillation of nasal drops, has been described, for example, in PCT Application Publication No. WO 2007/107789.

Methods of Treatment

In one aspect the present invention relates to a method of treating a subject suffering from a disorder associated with target gene expression comprising administering to the subject a therapeutically effective amount of a modified siRNA compound of the present invention. In preferred embodiments the subject being treated is a warm-blooded animal and, in particular, mammal including human.

"Treating a subject" refers to administering to the subject a therapeutic substance effective to ameliorate symptoms associated with a disease, to lessen the severity or cure the disease, to slow down the progress of the disease, to prevent the disease from occurring or to postpone the onset of the disease. "Treatment" refers to both therapeutic treatment and prophylactic or preventative measures, wherein the object is to prevent a disorder, to delay the onset of the disorder or reduce, the symptoms of a disorder. Those in need of treatment include those already experiencing the disease or condition, those prone to having the disease or condition, and those in which the disease or condition is to be prevented. The compounds of the invention are administered before, during or subsequent to the onset of the disease or condition.

A "therapeutically effective dose" refers to an amount of a pharmaceutical compound or composition which is effective to achieve an improvement in a subject or his physiological systems including, but not limited to, improved survival rate, more rapid recovery, improvement or elimination of symptoms, delayed onset of a disorder, slower progress of disease and other indicators as are selected as appropriate determining measures by those skilled in the art.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently. In various embodiments the present invention provides methods and compositions useful in preventing or treating primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, in a subject in need thereof.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, ischemic optic neuropathy (ION), anterior ischemic optic neuropathy (AION), optic neuritis (primary or secondary to autoimmune diseases), glaucoma, von Hippel Lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behçct's disease, sarcoidosis, coagulopathies, neuropathies, nephropathies, microvascular diseases of the kidney, and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. In various embodiments all these neovascular conditions are treated using the compounds and pharmaceutical compositions of the present invention.

"Eye disease" refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases and retinal vein occlusion (RVO). In various embodiments, conditions disclosed herein, such as DR, which are regarded as either a microvascular disorder and an eye disease, or both, under the definitions presented herein, are treated according to the methods of the present invention.

More specifically, the present invention provides methods and compositions useful in treating a subject suffering from or susceptible to adult respiratory distress syndrome (ARDS); Chronic obstructive pulmonary disease (COPD); acute lung injury (ALI); Emphysema; Diabetic Neuropathy, nephropathy and retinopathy; diabetic macular edema (DME) and other diabetic conditions; Glaucoma; age related macular degeneration (AMD); bone marrow transplantation (BMT) retinopathy, ischemic conditions; ocular ischemic syndrome (OIS); kidney disorders: acute renal failure (ARF), delayed graft function (DGF), transplant rejection; hearing disorders (including hearing loss); spinal cord injuries; oral mucositis; dry eye syndrome and pressure sores; neurological disorders arising from ischemic or hypoxic conditions, such as hypertension, hypertensive cerebral vascular disease, a constriction or obstruction of a blood vessel—as occurs in the case of a thrombus or embolus, angioma, blood dyscrasias, any form of compromised cardiac function including cardiac arrest or failure, systemic hypotension; stroke, disease, disorders and injury of the CNS, including, without being limited to, epilepsy, spinal cord injury, brain injury and neurodegenerative disorders, including, without being limited to Parkinson's disease, Amyotrophic Lateral Sclerosis (ALS, Lou Gehrig's Disease), Alzheimer's disease, Huntington's disease and any other disease-induced dementia (such as HIV-associated dementia for example).

The present invention relates to compounds, compositions and methods useful in the treatment of cancer. The terms "cancer" and "cancerous" refer to or describe the physiological condition in mammals that is typically characterized by unregulated cell growth. Examples of cancer include but are not limited, to, carcinoma, lymphoma, blastoma, sarcoma, and leukemia or lymphoid malignancies. Other examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosrcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

Fibrotic disorders include liver fibrosis, cirrhosis, pulmonary fibrosis including lung fibrosis (including ILF), kidney fibrosis resulting from any condition (e.g., CKD including ESRD), peritoneal fibrosis, chronic hepatic damage, fibrillogenesis, fibrotic diseases in other organs, abnormal scarring (keloids) associated with all possible types of skin injury accidental and jatrogenic (operations); scleroderma; cardiofibrosis, failure of glaucoma filtering operation; and intestinal adhesions.

Additionally, the invention provides a method of down-regulating the expression of a target gene by at least 20%, 30%, 40% or 50% as compared to a control comprising contacting target mRNA with one or more of the modified siRNA compounds of the present invention. In various embodiments the modified siRNA compound of the present invention down-regulates target gene whereby the down-regulation is selected from the group comprising down-regulation of gene function, down-regulation of polypeptide and down-regulation of mRNA expression.

The invention provides a method of inhibiting the expression of the target gene by at least 20%, 30%, or 40%, preferably by 50%, 60% or 70%, more preferably by 75%, 80% or 90% as compared to a control comprising contacting an mRNA transcript of the target gene with one or more of the modified siRNA compounds of the invention.

In one embodiment the modified siRNA compound of the invention inhibits the target gene polypeptide, whereby the inhibition is selected from the group comprising inhibition of function (which is examined by, for example, an enzymatic assay or a binding assay with a known interactor of the native gene/polypeptide, inter alia), inhibition of target protein (which is examined by, for example, Western blotting, ELISA or immunoprecipitation, inter alia) and inhibition of target mRNA expression (which is examined by, for example, Northern blotting, quantitative RT-PCR, in-situ hybridization or microarray hybridization, inter alia).

In additional embodiments the invention provides a method of treating a subject suffering from or susceptible to any disease or disorder accompanied by an elevated level of a mammalian or non-mammalian target gene, the method comprising administering to the subject a modified siRNA compound or composition of the invention in a therapeutically effective dose thereby treating the subject.

The present invention relates to the use of compounds which down-regulate the expression of a mammalian target gene particularly to modified RNA compounds according to structure (A) in the treatment of the following diseases or conditions in which inhibition of the expression of the mammalian target gene is beneficial: ARDS; COPD; ALI; Emphysema; Diabetic Neuropathy, nephropathy and retinopathy; DME and other diabetic conditions; Glaucoma; AMD; BMT retinopathy; ischemic conditions including stroke; OIS; Neurodegenerative disorders such as Parkinson's disease, Alzheimer's disease, ALS; kidney disorders: ARF, DGF, transplant rejection; hearing disorders; spinal cord injuries; oral mucositis; cancer including hematopoietic and solid tumor cancer, dry eye syndrome and pressure sores. In another embodiment the compounds of the present invention are useful in organ storage and/or preservation before transplant.

By "exposure to a toxic agent" is meant that the toxic agent is made available to, or comes into contact with, a mammal. A toxic agent can be toxic to the nervous system. Exposure to a toxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

In other embodiments the chemically modified siRNA compounds and methods of the invention are useful for treating or preventing the incidence or severity of other diseases and conditions in a subject. These diseases and conditions include, but are not limited to stroke and stroke-like situations (e.g. cerebral, renal, cardiac failure), neuronal cell death, brain injuries with or without reperfusion, spinal cord injury, chronic degenerative diseases e.g. neurodegenerative disease including, Alzheimer's disease, Parkinson's disease, Huntington's disease, multiple sclerosis, spinobulbar atrophy, prion disease and apoptosis resulting from traumatic brain injury (TBI). In an additional embodiment, the compounds and methods of the invention are directed to providing neuroprotection, and or cerebroprotection.

Without limitation a target gene is selected from the group consisting of p53 (TP53), TP53BP2, LRDD, CYBA, ATF3, CASP2 (Caspase 2), NOX3, HRK; C1QBP, BNIP3, MAPK8; Rac1, GSK3B, CD38, STEAP4, BMP2a; GJA1, TYROBP, CTGF, SPP1, RTN4R, ANXA2, RHOA, DUOX1, SLC5A1, SLC2A2, AKR1B1, SORD, SLC2A1, MME, NRF2, SRM, REDD2 (RTP801L), REDD1 (RTP801), NOX4, MYC, PLK1, ESPL1, HTRA2, KEAP1, p66, ZNHIT1, LGALS3, CYBB (NOX2), NOX1, NOXO1, ADRB1, HI 95, ARF1, ASPP1, SOX9, FAS, FASLG, Human MLL, AF9, CTSD, CAPNS1, CD80, CD86, HES1, HES5, CDKN1B, ID1, ID2, ID3, CDKN2A, Caspase 1, Caspase 3, Caspase 4, Caspase 5, Caspase 6, Caspase 7, Caspase 8, Caspase 9, Caspase 10, Caspase 12, Caspase 14, Apaf-1, Nod1, Nod2, Ipaf, DEFCAP, RAIDD, RICK, Bcl10, ASC, TUCAN, ARC, CLARP, FADD, DEDD, DEDD2, Cryopirin, PYC1, Pyrin, TRADD, UNC5a, UNC5b, UNC5c, ZUD, p84N5, LRDD, CDK1, CDK2, CDK4, CDK5, CDK9, PITSLRE A, CHK2, LATS1, Prk, MAP4K1, MAP4K2, STK4, SLK, GSK3alpha, GSK3beta, MEKK1, MAP3K5 (Ask1), MAP3K7, MAP3K8, MAP3K9, MAP3K10, MAP3K11, MAP3K12, DRP-1, MKK6, p38, JNK3, DAPK1, DRAK1, DRAK2, IRAK, RIP, RIP3, RIP5, PKR, IRE1, MSK1, PKCalpha, PKCbeta, PKCdelta, PKCepsilon, PKCeta, PKCmu, PKCtheta, PKCzeta, CAMK2A, HIPK2, LKB1, BTK, c-Src, FYN, Lck, ABL2, ZAP70, TrkA, TrkC, MYLK, FGFR2, EphA2, AATYK, c-Met, RET, PRKAA2, PLA2G2A, SMPD1, SMPD2, SPP1, FAN, PLCG2, IP6K2, PTEN, SHIP, AIF, AMID, Cytochrome c, Smac, HtrA2, TSAP6, DAP-1, FEM-, DAP-3, Granzyme B, DIO-1, DAXX, CAD, CIDE-A, CIDE-B, Fsp27, Ape1, ERCC2, ERCC3, BAP31, Bit1, AES, Huntingtin, HIP1, hSir2, PHAP1, GADD45b, GADD34, RAD21, MSH6, ADAR, MBD4, WW45, ATM, mTOR, TIP49, diubiquitin/FAT10, FAF1, p193, Scythe/BAT3, Amida, IGFBP-3, TDAG51, MCG10, PACT, p52/RAP, ALG2, ALG3, presenelin-1, PSAP, AIP1/Alix, ES18, mda-7, p14ARF, ANT1, p33ING1, p33ING2, p53AIP1, p53DINP1, MGC35083, NRAGE, GRIM19, lipocalin 2, glycodelin A, NADE, Porimin, STAG1, DAB2, Galectin-7, Galectin-9, SPRC, FLJ21908, WWOX, XK, DICK-1, Fzd1, Fzd2, SARP2, axin 1, RGS3, DVL1, NFkB2, IkBalpha, NF-ATC1, NF-ATC2, NF-ATC4, zf3/ZNF319, Egr1, Egr2, Egr3, Sp1, TIEG, WT1, Zac1, Icaros, ZNF148, ZK1/ZNF443, ZNF274, WIG1, HIVEP1, HIVEP3, Fliz1, ZPR9, GATA3, TR3, PPARG, CSMF, RXRa, RARa, RARb, RARg, T3Ra, Erbeta, VDR, GR/GCCR, p53, p73alpha, p63 (human [ta alpha, ta beta, ta gamma, da alpha, a beta, da gamma], 53BP2, ASPP1, E2F1, E2F2, E2F3, HIF1 alpha, TCF4, c-Myc, Max, Mad, MITF, Id2, Id3, Id4, c-Jun, c-Fos, ATF3, NF-IL6, CHOP, NRF1, c-Maf, Bach2, Msx2, Csx, Hoxa5, Ets-1, PU1/Spi1, Ets-2, ELK1, TEL1, c-Myb, TBX5, IRF1, IRF3, IRF4, IRF9, AP-2 Ipha, FKHR, FOXO1A, FKHRL1, FOXO3a, AFX1, MLLT7, Tip60, BTG1, ALF1, HNRPD, TIA1, NDG1, PCBP4, MCG10, FXR2, TNFR2, LTbR, CD40, CD27, CD30, 4-IBB, INFRSF19, XEDAR, Fn14, OPG, DcR3, FAS, TNFR1, WSL-1, p75NTR, DR4, DR5, DR6, EDAR, TNF Ipha, FAS ligand, TRAIL, Lymphotoxin alpha, Lymphotoxin beta, 4-1BBL, RANKL, TL1, TWEAK, LIGHT, APRIL, IL-1-alpha, IL-1-beta, IL-18, FGF, IL-2, IL-21, IL-5, IL-4, IL-6, LIF, IL-12, IL-7, IL-10, IL-19, IL-24, IFN alpha, IFN beta, IFN gamma, M-CSF, Prolactinm, TLR2, TLR3, TLR4, MyD88, TRIF, RIG-1, CD14, TCR alpha, CD3 gamma, CD8, CD4, CD7, CD19, CD28, CTLA4, SEMA3A, SEMA3B, HLA-A, HLA-B, HLA-L, HLA-Dmalpha, CD22, CD33, CALL, DCC, ICAM1, ICAM3, CD66a, PVR, CD47, CD2, Thy-1, SIRPa1, CD5, E-cadherin, ITGAM, ITGAV, CD18, ITGB3, CD9, IgE Fc R beta, CD82, CD81, PERP, CD24, CD69, KLRD1, galectin 1, B4GALT1, C1q alpha, C5R1, MIP1alpha, MIP1beta, RANTES, SDF1, XCL1, CCCKR5, OIAS/OAS1, INDO, MxA, IFI16, AIM2, iNOS, HB-EGF, HGF, MIF, TRAF3, TRAF4, TRAF6, PAR-4, IKKGamma, FIP2, TXBP151, FLASH, TRF1, IEX-1S, Dok1, BLNK, CIN85, Bif-1, HEF1, Vav1, RasGRP1, POSH, Rac1, RhoA, RhoB, RhoC, ALG4, SPP1, TRIP, SIVA, TRABID, TSC-22, BRCA1, BARD1, 53BP1, MDC1, Mdm4, Siah-1, Siah-2, RoRet, TRIM35, PML, RFWD1, DIP1, Socs1, PARC, USP7, CYLD, SERPINH1 (HSP47). Other useful target genes are genes of microbial origin.

Combination Therapy

The methods of treating the diseases disclosed herein include administering a modified double stranded nucleic acid molecule disclosed herein in conjunction or in combination with an additional inhibitor, a substance which improves the pharmacological properties of the modified siRNA compound, or an additional compound known to be effective in the treatment of a subject suffering from or susceptible to any of the hereinabove mentioned diseases and disorders, including microvascular disorder, eye disease and condition (e.g. macular degeneration), hearing impairment (including hearing loss), respiratory disorder, kidney disorder, organ transplantation, neurodegenerative disorder, spinal cord injury, brain injury, angiogenesis- and apoptosis-related condition.

The present invention thus provides in another aspect, a pharmaceutical composition comprising a combination of a therapeutic modified siRNA compound of the invention together with at least one additional therapeutically active agent. By "in conjunction with" or "in combination with" is meant prior to, simultaneously or subsequent to. Accordingly, the individual components of such a combination are administered either sequentially or simultaneously from the same or separate pharmaceutical formulations.

Combination therapies comprising known treatments for treating microvascular disorders, eye disease and conditions (e.g. macular degeneration), hearing impairments (including hearing loss), respiratory disorders, kidney disorders, organ transplantation, neurodegenerative disorders (e.g. spinal cord injury), angiogenesis- and apoptosis-related conditions, in conjunction with the modified siRNA compounds and therapies described herein are considered part of the current invention.

Accordingly, in another aspect of present invention, an additional pharmaceutically effective compound is administered in conjunction with the pharmaceutical composition of the invention. In addition, the modified siRNA compounds of the invention are used in the preparation of a medicament for use as adjunctive therapy with a second therapeutically active compound to treat such conditions. Appropriate doses of known second therapeutic agents for use in combination with a chemically modified siRNA compound of the invention are readily appreciated by those skilled in the art.

In some embodiments the combinations referred to above are presented for use in the form of a single pharmaceutical formulation.

The administration of a pharmaceutical composition comprising any one of the pharmaceutically active siRNA conjugates according to the invention is carried out by any of the many known routes of administration, including intravenously, intra-arterially, subcutaneously, intra-peritoneally or intra-cerebrally, as determined by a skilled practitioner. Using specialized formulations, it is possible to administer the compositions orally or via inhalation or via intranasal instillation. In some embodiments a compound of the present invention is formulated for topical administration, including as eardrops, eye drops, dermal formulation, transdermal formulation and the like.

By "in conjunction with" is meant that the additional pharmaceutically effective compound is administered prior to, at the same time as, or subsequent to administration of the compounds or the pharmaceutical compositions of the present invention. The individual components of such a combination referred to above, therefore, can be administered either sequentially or simultaneously from the same or separate pharmaceutical formulations. As is the case for the present modified siRNA compounds, a second therapeutic agent can be administered by any suitable route, for example, by oral, buccal, inhalation, sublingual, rectal, vaginal, transurethral, nasal, otic, ocular, topical, percutaneous (i.e., transdermal), or parenteral (including intravenous, intramuscular, subcutaneous, and intracoronary) administration.

In some embodiments, a modified siRNA compound of the invention and the second therapeutic agent are administered by the same route, either provided in a single composition as two or more different pharmaceutical compositions. However, in other embodiments, a different route of administration for the modified siRNA compound of the invention and the second therapeutic agent is either possible or preferred. Persons skilled in the art are aware of the best modes of administration for each therapeutic agent, either alone or in combination.

In various embodiments, the modified siRNA compounds of the present invention are the main active component in a pharmaceutical composition.

In another aspects, the present invention provides a pharmaceutical composition comprising two or more siRNA molecules for the treatment of a disease and for any of the diseases and conditions mentioned herein. In some embodiments the two or more siRNA molecules or formulations comprising said molecules are admixed in the pharmaceutical composition in amounts that generate equal or otherwise beneficial activity. In certain embodiments the two or more siRNA molecules are covalently or non-covalently bound, or joined together by a nucleic acid linker of a length ranging from 2-100, preferably 2-50 or 2-30 nucleotides.

In some embodiments the pharmaceutical compositions of the invention further comprise one or more additional siRNA molecule, which targets one or more additional gene. In some embodiments, simultaneous inhibition of said additional gene(s) provides an additive or synergistic effect for treatment of the diseases disclosed herein.

The treatment regimen according to the invention is carried out, in terms of administration mode, timing of the administration, and dosage, so that the functional recovery of the patient from the adverse consequences of the conditions disclosed herein is improved or so as to postpone the onset of a disorder.

The invention has been described in an illustrative manner, and it is to be understood that the terminology used is intended to be in the nature of words of description rather than of limitation.

Modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al, Blood 1996, 87:3822.) Methods of performing RT-PCR are also well known in the art.

generated. In addition to the algorithm, some 23-mer oligomer sequences are generated by 5' and/or 3' extension of the 19-mer sequences. The antisense strand sequences that were generated using this method are fully or substantially complementary to a section of target mRNA sequence. In some embodiments the antisense sequence is fully complementary to a section of the corresponding mRNA sequence. For generating the modified siRNA compounds of the invention, the nucleotide at the 5' terminal position of the antisense strand (N)x (position 1; $N^1$) was substituted to generate a double stranded nucleic acid molecule of embodiments of structure (A). In other examples, the nucleotide at the 5' terminal position of the antisense strand (N)x and the nucleotide at the 3' terminal position of the sense strand (N')y were substituted to generate the double stranded nucleic acid molecule of embodiments of structure (A).

Table A provides nucleotide sequences of sense and antisense strands of compounds used in some of examples. Table A1 provides exemplary double stranded nucleic acid molecules that were generated as described to provide modified siRNA compounds according to embodiments of structure (A). The compounds shown herein are not meant to be limiting and any target RNA my be used to identify double stranded nucleic acid molecules as described herein. Table A2 provides modified siRNA compounds that were generated for comparative testing. The modified siRNA compounds in Tables A1 and A2 target TLR2 (*Homo sapiens* toll-like receptor 2 (TLR2), mRNA, gi|68160956|ref|NM_003264.3|, SEQ ID NO:4) gene and CAINS1 (calpain, small subunit 1 variant gi|51599152|ref|NM_001749.2|; SEQ ID NO:1 or calpain, small subunit 1 variant 2 gi|51599150|ref|NM_001003962.1|, SEQ ID NO:2) gene. Additional compounds target human RhoA mRNA (ras homolog gene family, member A (RhoA), mRNA gi|50593005 |ref|NM_001664.2|, SEQ D) NO:3). mRNA sequences of mammalian target genes are available, for example, on the NCBI web site [http://www.ncbi.nlm.nih.gov/].

TABLE 1

| dsRNA molecule | SEQ ID | SENSE | SEQ ID | ANTISENSE |
|---|---|---|---|---|
| CAPNS1_23 | 5 | GAGAUGACAUGGAGGUCAG | 10 | CUGACCUCCAUGUCAUCUC |
| TLR2_16 | 6 | GAGUGGUGCAAGUAUGAAC | 11 | GUUCAUACUUGCACCACUC |
| TLR2_37 | 7 | GGUGGAGAACCUUAUGGUC | 12 | GACCAUAAGGUUCUCCACC |
| TLR2_46 | 8 | AGAUAAUGAACACCAAGAC | 13 | GUCUUGGUGUUCAUUAUCU |
| RHOA_61 | 9 | GAUCUUCGGAAUGAUGAGA | 14 | UCUCAUCAUUCCGAAGAUC |

Example 1

Generation of Sequences for siRNAs to Target Genes and Production of the Modified siRNA Compounds Using proprietary algorithms and the known sequence of any gene, optionally the pro-apoptotic genes disclosed herein, t19-mer sequences of many potential siRNAs were

TABLE A1

Exemplary TLR2 double stranded molecules of the invention
siRNA Compund
(N')y
(N)x

| TLR2_16_S1016 | SEN | 5' G̲AG̲UG̲G̲UG̲C̲AAG̲UAUG̲AAG 3' |
| | AS | 5' UUUCAUACUUGCACCACUC 3' |
| TLR2_16_S1018 | SEN | 5' G̲AG̲UG̲G̲UG̲C̲AAG̲UAUG̲AAG 3' |
| | AS | 5' CUUCAUACUUGCACCACUC 3' |

TABLE A1-continued

Exemplary TLR2 double stranded molecules of the invention
siRNA Compund
(N')y
(N)x

| | | | |
|---|---|---|---|
| TLR2_16_S1019 | SEN | 5' | GAGUGGUGCAAGUAUGAAG 3' |
| | AS | 5' | dUUUCAUACUUGCACCACUC 3' |
| TLR2_16_S1020 | SEN | 5' | GAGUGGUGCAAGUAUGAAG 3' |
| | AS | 5' | dBUUCAUACUUGCACCACUC 3' |
| TLR2_16_S1022 | SEN | 5' | GAGUGGUGCAAGUAUGAAU 3' |
| | AS | 5' | UUUCAUACUUGCACCACUC 3' |
| TLR2_16_S1024 | SEN | 5' | GAGUGGUGCAAGUAUGAAU 3' |
| | AS | 5' | CUUCAUACUUGCACCACUC 3' |
| TLR2_16_S1025 | SEN | 5' | GAGUGGUGCAAGUAUGAAU 3' |
| | AS | 5' | dUUUCAUACUUGCACCACUC 3' |
| TLR2_16_S1026 | SEN | 5' | GAGUGGUGCAAGUAUGAAU 3' |
| | AS | 5' | dBUUCAUACUUGCACCACUC 3' |
| TLR2_16_S1028 | SEN | 5' | GAGUGGUGCAAGUAUGAAC 3' |
| | AS | 5' | CUUCAUACUUGCACCACUC 3' |
| TLR2_16_S1029 | SEN | 5' | GAGUGGUGCAAGUAUGAAC 3' |
| | AS | 5' | dUUUCAUACUUGCACCACUC 3' |
| TLR2_16_S1030 | SEN | 5' | GAGUGGUGCAAGUAUGAAC 3' |
| | AS | 5' | dBUUCAUACUUGCACCACUC 3' |
| TLR2_16_S1032 | SEN | 5' | GAGUGGUGCAAGUAUGAAA 3' |
| | as | 5' | CUUCAUACUUGCACCACUC 3' |
| TLR2_16_S1033 | SEN | 5' | GAGUGGUGCAAGUAUGAAA 3' |
| | AS | 5' | dUUUCAUACUUGCACCACUC 3' |
| TLR2_16_S1034 | SEN | 5' | GAGUGGUGCAAGUAUGAAA 3' |
| | AS | 5' | dBUUCAUACUUGCACCACUC 3' |
| TLR2_16_S941 | SEN | 5' | GAGUGGUGCAAGUAUGAAC 3' |
| | AS | 5' | UUUCAUACUUGCACCACUC 3' |
| TLR2_16_S938 | SEN | 5' | GAGUGGUGCAAGUAUGAAA 3' |
| | AS | 5' | UUUCAUACUUGCACCACUC 3' |
| CAPNS1_23_S938 | SEN | 5' | GAGAUGACAUGGAGGUCAA 3' |
| | AS | 5' | UUGACCUCCAUGUCAUCUC 3' |
| CAPNS1_23_S898 | SEN | 5' | GAGAUGACAUGGAGGUCAA 3' |
| | AS | 5' | UUGACCUCCAUGUCAUCUC-dTdT 3' |
| CAPNS1_23_S939 | SEN | 5' | GAGAUGACAUGGAGGUCAA 3' |
| | AS | 5' | CUGACCUCCAUGUCAUCUC 3' |

TABLE A2

Compounds that were synthesized for comparative testing
siRNA Compound
(N')y
(N)x

| | | | |
|---|---|---|---|
| TLR2_16_S1015 | SEN | 5' | GAGUGGUGCAAGUAUGAAG 3' |
| | AS | 5' | GUUCAUACUUGCACCACUC 3' |
| TLR2_16_S1017 | SEN | 5' | GAGUGGUGCAAGUAUGAAG 3' |
| | AS | 5' | AUUCAUACUUGCACCACUC 3' |
| TLR2_16_S1021 | SEN | 5' | GAGUGGUGCAAGUAUGAAU 3' |
| | AS | 5' | GUUCAUACUUGCACCACUC 3' |
| TLR2_16_S1023 | SEN | 5' | GAGUGGUGCAAGUAUGAAU 3' |
| | AS | 5' | AUUCAUACUUGCACCACUC 3' |

TABLE A2-continued

Compounds that were synthesized for comparative testing
siRNA Compound
(N')y
(N)x

| | | | |
|---|---|---|---|
| TLR2_16_S1027 | SEN | 5' | GAGUGGUGCAAGUAUGAAC 3' |
| | AS | 5' | AUUCAUACUUGCACCACUC 3' |
| TLR2_16_S1031 | SEN | 5' | GAGUGGUGCAAGUAUGAAA 3' |
| | AS | 5' | AUUCAUACUUGCACCACUC 3' |
| TLR2_16_S73 | SEN | 5' | GAGUGGUGCAAGUAUGAAC 3' |
| | AS | 5' | GUUCAUACUUGCACCACUC 3' |
| TLR2_16_S939 | SEN | 5' | GAGUGGUGCAAGUAUGAAA 3' |
| | AS | 5' | GUUCAUACUUGCACCACUC 3' |
| CAPNS1_23_S73 | SEN | 5' | GAGAUGACAUGGAGGUCAG 3' |
| | AS | 5' | CUGACCUCCAUGUCAUCUC 3' |
| CAPNS1_23_S867 | SEN | 5' | GAGAUGACAUGGAGGUCAG 3' |
| | AS | 5' | CUGACCUCCAUGUCAUCUC-dTdT 3' |

Table A3 hereinbelow provides a code of the modified nucleotides/unconventional moieties utilized in preparing the siRNA oligonucleotides of Tables A1 and A2.

TABLE A3

Code of the modified nucleotides/unconventional moieties as used in the Tables herein.

| Code | Modification |
|---|---|
| dT | thymidine-3'-phosphate |
| A | 2'-O-methyladenosine-3'-phosphate |
| C | 2'-O-methylcytidine-3'-phosphate |
| G | 2'-O-methylguanosine-3'-phosphate |
| U | 2'-O-methyluridine-3'-phosphate |
| dB | Inverted abasic deoxyribose-3'-phosphate |
| dU | deoxyribouridine-3'-phosphate |
| LdC | L-deoxyribocytidine-3'-phosphate (enantiomeric dC) |
| C3 | C3-OH |
| C3C3 | C3Pi-C3OH |

Example 2

In Vitro Testing of Modified siRNA Compounds

Protocol for Testing siRNA Activity

The modified siRNA compounds according to the present invention are tested for activity as follows: About $1 \times 10^5$ rat REF52 (for TLR2 siRNA activity) or $0.6 \times 10^5$ human PC3 cells (for CAPNS1 siRNA activity) were seeded per well in 6 wells plate (30-70% confluent). After about 24 h incubation, cells were transfected with dsRNA oligos (see Tables A4 and A5 below), using Lipofectamine™2000 (Invitrogene) at final concentrations of 1-40 nM for TLR2 dsRNA and at final concentrations of 5-40 nM for CAPNS1 dsRNA

TABLE A4

TLR2_16 siRNA compounds (SEQ ID NOS: 6 and 11)

| | | | | |
|---|---|---|---|---|
| TLR2_16_S73 (control compound) | SEN 5' | GAGUGGUGCAAGUAUGAAC | 3' | G-C base pair. |
| | AS 5' | GUUCAUACUUGCACCACUC | 3' | AS full match to target |
| TLR2_16_S941 | SEN 5' | GAGUGGUGCAAGUAUGAAC | 3' | U-C. AS mismatch to target |
| | AS 5' | ⓊUUCAUACUUGCACCACUC | 3' | |
| TLR2_16_S939 | SEN 5' | GAGUGGUGCAAGUAUGAA | 3' | G-A. AS match to target. Mismatch in duplex |
| | AS 5' | GUUCAUACUUGCACCACUC | 3' | |
| TLR2_16_S938 | SEN 5' | GAGUGGUGCAAGUAUGAAA | 3' | U-A base pair. AS mismatch to target |
| | AS 5' | ⓊUUCAUACUUGCACCACUC | 3' | |

TABLE A5

CAPNS1_23 siRNA compounds (SEQ ID NOS: 5 and 10)

| | | | |
|---|---|---|---|
| CAPNS1_23_S73 (control compound) | SEN 5' | GAGAUGACAUGGAGGUCAG 3' | C-G base pair. AS full match to target |
| | AS 5' | CUGACCUCCAUGUCAUCUC 3' | |
| CAPNS1_23_S867 | SEN 5' | GAGAUGACAUGGAGGUCAG 3' | C-G base pair. AS full match to target |
| | AS 5' | CUGACCUCCAUGUCAUCUC-dTdT 3' | |
| CAPNS1_23_S938 | SEN 5' | GAGAUGACAUGGAGGUCA 3' | U-A base pair. AS mismatch to target |
| | AS 5' | ⓊUGACCUCCAUGUCAUCUC 3' | |
| CAPNS1_23_S939 | SEN 5' | GAGAUGACAUGGAGGUCA 3' | C-A. AS full match to target |
| | AS 5' | CUGACCUCCAUGUCAUCUC 3' | |

As positive control for cell transfection efficiency, REDD14-Cy3.5 labeled oligos were used. As negative control for siRNA activity scrambled (CNL) oligos were used (same concentration as mentioned in section 1.2). Transfection efficiency was tested by fluorescent microscopy, 24 hrs following cell transfection.

siRNA Sample preparation: For each transfected well 3 μl Lipofectamine2000 reagent was diluted in 250 μl serum free medium, and incubate for 5 min at RT.

siRNA molecules were prepared as follows:
siRNA Working Solution:
REDD14-Cy3.5 stock 1.5×10$^6$ nM (dilute 1:150 to have final concentration of 10 μM with PBS)
CNL stock 1.6×10$^6$ nM (dilute 1:160 to have final concentration of 10 μM with PBS)
Target genes stock 100 μM (dilute 1:10 to have final concentration of 10 μM with PBS)
Samples were diluted to final concentration for TLR2, CAPNS1 and CNL siRNA oligos as mentioned above (section 1.2 and 1.4) and 20 nM of REDD14-Cy3.5 siRNA in 250 DMEM medium, calculated to final volume of 2 ml per well. Lipofectamine™ 2000 was combined with siRNA (1:1 volume), sample was mixed gently and incubated at room temperature for 20 minutes.

Transfection: The Lipofectamine/siRNA complex was added onto the cells (500 μl per well), the plate was rocked back and forth (2 ml final volume in each well). Cells were incubated at 37° C. in a $CO_2$ incubator.

Quantification of mRNA levels by qPCR: 48 hrs following cells transfection, cells were harvested and RNA was isolated using EZ-RNA™ kit [Biological Industries (#20-410-100). cDNA Synthesis was performed and mRNA level of was measured by qPCR.

Measured mRNA quantities were normalized to the mRNA quantity of the reference gene peptidylprolyl isomerase A (cyclophilin A; CycloA)

siRNA Activity Results:

TLR2_16 siRNA activity: qPCR analysis of rat TLR2 expression in REF52 cells expressing endogenous gene, following TLR2_16 siRNA transfection (data in Table A6 demonstrate residual (% of Ctrl-un-transfected cells) rat TLR2 expression in REF52 cells.

TABLE A6

| | | Exp1 | Exp2 | Exp3 | Exp4 | Exp5 | Average | Sd |
|---|---|---|---|---|---|---|---|---|
| Control | | 100 | 100 | 100 | 100 | 100 | 100 | 0 |
| CNL | 40 nM | 131 | | | 131 | | 131 | 0 |
| | 20 nM | 115 | 84 | | 97 | 89 | 96 | 12 |
| | 5 nM | | 101 | | | 102 | 102 | 0 |

TABLE A6-continued

|  |  | Exp1 | Exp2 | Exp3 | Exp4 | Exp5 | Average | Sd |
|---|---|---|---|---|---|---|---|---|
| TLR2_16_S73 | 40 nM | 22 |  |  | 26 | 13 | 20 | 6 |
| G-C base pair. AS full match to target | 20 nM | 35 | 17 |  | 17 |  | 23 | 9 |
| TLR2_16_S938 | 40 nM | 17 |  |  | 16 | 3 | 12 | 6 |
| U- A base pair. AS mismatch to target | 20 nM | 13 | 18 |  | 24 |  | 19 | 5 |
|  | 5 nM |  | 24 |  | 52 |  | 38 | 14 |
|  | 1 nM |  | 52 |  | 15 |  | 33 | 19 |
| TLR2_16_S939 | 40 nM | 15 |  |  | 32 | 10 | 19 | 10 |
| G-A. AS match to target. Mismatch in duplex | 20 nM | 26 | 39 |  | 57 |  | 41 | 13 |
|  | 5 nM |  | 57 |  | 50 |  | 53 | 4 |
|  | 1 nM |  | 50 |  | 7 |  | 29 | 21 |
| TLR2_16_S941 | 40 nM | 7 |  |  | 18 |  | 13 | 5 |
| U-C. AS mismatch to target. Duplex mismatch | 20 nM |  | 18 | 26 | 132 |  | 59 | 52 |
|  | 5 nM |  | 132 | 28 |  |  | 80 | 52 |

The most active compound was TLR2_16_S938 which has AS mismatch to target mRNA and fully complementary duplex. In TLR2_16_S938 $N^1$=U and $N^2$=A and $N^1$ is mismatched to C in target mRNA.

CAPNS1_23 siRNA Activity qPCR analysis of CAPNS1 expression in human PC-3 cells expressing endogenous gene, following CAPNS1_23 siRNA transfection (data in Table A7 demonstrate residual (% of Ctrl-un-transfected cells) human CAPNS1 expression in PC-3 cells.

TABLE A7

|  |  | Exp 1 |
|---|---|---|
| Control |  | 100 |
| CNL | 40 nM | 147 |
|  | 20 nM | 132 |
|  | 5 nM | 133 |
| CAPNS1_23_S73 | 40 nM | 32 |
| C-G base pair, AS full match to target | 20 nM | 29 |
|  | 5 nM | 43 |
| CAPNS1_23_S867 | 40 nM | 43 |
| C-G base pair, AS full match to target | 20 nM | 24 |
|  | 5 nM | 38 |
| CAPNS1_23_S938 | 40 nM | 27 |
| U-A base pair, AS mismatch to target. | 20 nM | 14 |
|  | 5 nM | 22 |
| CAPNS1_23_S939 | 40 nM | 28 |
| C-A. AS full match to target | 20 nM | 29 |
| Duplex mismatch | 5 nM | 13 |

The most active compound was CAPNS1_23_S938 which has AS mismatch to target mRNA and fully complementary duplex. In CAPNS1_23_S938 $N^1$=U and $N^2$=A and $N^1$ is mismatched to C in target mRNA.

The test compounds according to Structure (A) structures, are at least 10% more active than the control compounds, wherein the antisense strand is fully complementary to the target mRNA.

On-Target and Off-Target Testing of Double-Stranded RNA Molecules

The purpose of this study was to assess the on-target activity and potential off-target activity of control (unmodified) and test (chemically modified) double stranded nucleic acid molecules.

The two strands of a siRNA molecule have sequences with configurations that are sense and antisense with respect to the target gene mRNA. Within a cell, the antisense strand of siRNA, known as the guide strand (GS) is loaded into the RNA-induced silencing complex (RISC) and serves to guide the RNAi machinery to complementary sequences in target mRNA. The sense strand, known as the passenger strand (PS), is destroyed. When exact complementarity exists between the (GS and the target mRNA the latter is cleaved by the RNaseH-like slicer activity of RISC.

In some cases a siRNA molecule may down-regulate unintended genes whose transcripts possess complementarity to the GS seed region (nucleotides at positions 2-8 [5'>3']) in the 3'-UTR. Without wishing to be bound to theory, this off-target effect may be mediated by a mechanism similar to that of target silencing by microRNAs (miRNAs). Another type of off-target activity of siRNA may occur due to loading of the sense strand (PS) into RISC. The unintended off-target effects of synthetic siRNAs can be reduced or abrogated by chemical modification of the initial siRNA sequence in the siRNA duplex. The test molecules were designed accordingly.

Test molecules were assessed for both on-target activity (activity to target mRNA) and off-target activity (activity to mRNA other than target mRNA) in the "guide-seed-sequence-and-passenger-strand-based activity assay" using the psiCHECK™ (Promega) plasmid constructs. The activity of test and control molecules was tested against either a full target sequence (nucleotide sequence fully complementary to the whole 19-base sequence of either the GS or PS of test molecule) or the seed-target sequence (sequence complementary to nucleotides 1-8 [5'>3'] of either the GS or PS of test molecule).

The test molecules were at least as active against the GS full target site than was the non-modified control siRNA. Test molecules were inactive towards the PS full target site, whereas the control non-modified siRNA demonstrated activity towards the same site.

Both siRNAs were inactive against the GS seed-target sequence and the PS seed-target sequence sites.

Guide strand (GS) refers to the antisense strand of a double stranded RNA that is able to enter the RISC complex and guide silencing of the target RNA.

Passenger strand (PS) refers to the sense strand of a double stranded RNA.

Seed sequence refers to nucleotides 2-8 (5'>3') of the GS and relevant for the off-target recognition.

CM (complete match) refers to a synthetic DNA fragment with nucleotide sequence fully complementary to the guide strand of the double stranded RNA molecule. This DNA fragment is cloned in 3'UTR of a reporter gene and serves as a target for RNA silencing. (Castanotto & Rossi (2009). Nature, 22:426-33).

SM (seed match) refers to a synthetic DNA fragment with nucleotide sequence with full complementarity to the nucleotides 1-8 (5'>3') of the guide strand of the test molecule siRNA (1st nucleotide+seed). This DNA fragment is cloned in 3'UTR of a reporter gene and serves as a target for the seed-based "off-target" silencing.

The psiCHECK™ system enables evaluation of the GS (antisense) and the PS (sense strand) to elicit targeted and off-targeted effects, by monitoring the changes in expression levels of their target sequences. Four psiCHECK™-2-based (Promega) constructs were prepared for the evaluation of target activity and potential off-target activity of each test molecule GS and PS strands. In each of the constructs one copy or three copies of either the full target or the seed-target sequence, of test molecule PS or GS, was cloned into the multiple cloning site located downstream of the Renilla luciferase translational stop codon in the 3'-UTR region. The resulting vectors were termed:

1—GS-CM (guide strand, complete-match) vector containing one copy or three copies of the full target sequence (nucleotide sequence fully complementary to the whole 19-base sequence of the GS of the test molecule);

2—PS-CM (passenger strand, complete-match) vector containing one copy or three copies of the full target sequence (nucleotide sequence fully complementary to the whole 19-base sequence of the PS of the test molecule);

3—GS-SM (guide strand, seed-match) vector containing one copy or three copies of the seed region target sequence (sequence complementary to nucleotides 1-8 of the GS of the test molecule);

4—PS-SM (passenger strand, geed-match) vector containing one copy or three copies of the seed region target sequence (sequence complementary to nucleotides 1-8 of the PS of the test molecule).

The target sequences, with or without nucleotide substitutions at position 19 (position 1 of AS) were cloned downstream to the coding region of the Renilla luciferase reporter gene. The RNAi or seed-mediated activity of a test molecule toward any of these sequences results either in cleavage and subsequent degradation of the fusion mRNA (GS) or in translational inhibition (PS). In both cases protein expression is attenuated.

Cloning of Test Molecule GS and PS Seed and Full Target Sites

A single copy of the relevant target cloned in the 3'UTR of the reporter mRNA, Renilla Luciferase in the psiCHECK™-2 (Promega) vector. There are multiple cloning sites in the vector. Typical cloning sites that were used are XhoI and NotI. Vector was prepared for cloning using standard molecular biology techniques. Each strand of CM and SM was chemically synthesized and annealed by heating to 100° C. and cooled to room temperature. Ligation was carried out for 3 hours using standard molecular biology techniques. Ligated plasmids were transformed into E. coli DH5a cells Resulting colonies were screened for presence of plasmid constructs by colony-PCR using relevant primers. Each of the plasmids (vectors) was purified from one positive colony and its sequence was verified.

Transfection of Vectors into Human HeLa Cells.

About 1.3-2×10$^6$ human HeLa cells (ATCC, Cat#CCL-2) were inoculated per 10 cm dish. Cells were then incubated in 37±1° C., 5% $CO_2$ for 24 hours. Growth medium was replaced one day post inoculation by 8 mL fresh growth medium prepared. Each cell-containing plate was transfected with one of the vectors, using Lipofectamine™2000 reagent (Invitrogen) as follows:

In an Eppendorf tube, 15 μL Lipofectamine™2000 reagent was diluted in 1000 μL DMEM medium and incubated for 5 minutes at room temperature (RT). In a second Eppendorf tube, a vector was diluted to reach a final concentration of 15 μg in 1000 μL DMEM medium. The diluted Lipofectamine™2000 reagent was mixed gently with the diluted DNA vector sample and incubated for 20-40 minutes at RT. Following incubation, DNA/Lipofectamine™2000 was added (to reach a 2000 μL final volume) to the cells. The plates were gently rocked. Plates were incubated for 5 hours at 37±1° C. and 5% $CO_2$. Following a 5-hour incubation, cells were re-plated in a 96-well plate at final concentration of 5×10 cells per well in 80 μL growth medium. 16 hours later, cells were transfected with test or control molecules using Lipofectamine™2000. Duplicate transfections of each siRNA concentration were performed, as described below:

Lipofectamine™2000 was prepared in excess to suffice for 170 wells: 85 μL of Lipofectamine™2000 were mixed with 3400 μL (3.4 mL) of DMEM medium and incubated for 5 minutes at RT.

Preparation of test and control molecule working solutions: working solutions at various concentrations was prepared by diluting a 10 μM stock solution. This dilution series was prepared for the generation of final transfection concentrations ranging between 0.0095 nM and 100 nM in 100 μL DMEM transfection medium (0.0095, 0.019, 0.039, 0.07, 0.15, 0.31, 0.625, 1.25, 2.5, 5.0, 20.0, 100.0).

100 μL aliquots of the diluted Lipofectamine 2000 were mixed gently with 100 μL of each of the diluted test molecule or control molecule working solutions (above) and mixtures were incubated for 20-40 minutes at RT. Following incubation, 20 μL of the siRNA/Lipofectamine™2000 mixture were added on top of the cells (pre-incubated with 80 μL of cell-culture medium above). The plates were gently rocked. Cells were incubated for 48 hours at 37±1° C. and 5% $CO_2$.

Determination of Renilla Luciferase Activity in Transfected Cells

The psiCHECK™-2 vector enables monitoring of changes in expression of a target sequence fused to the Renilla luciferase reporter gene. The test/control molecule target sequence is cloned into the 3'-untranslated region (3'-UTR) of Renilla luciferase. Measuring the decrease in Renilla luciferase activity thus provides a convenient way of monitoring activity. In addition, the psiCHECK™-2 vector contains a second reporter gene, Firefly luciferase, transcribed under a different promoter, which allows for normalization of Renilla luciferase expression.

48 Hours following test or control molecule, transfection Renilla and FireFly Luciferase activities were measured in each of the siRNA transfected samples, using Dual-Luciferase® Assay kit (Promega) according to manufacturer procedure:

Medium was completely removed from cells and cells were then lysed by the addition of 40 μL/well 1× Luciferase lysis solution. Plates were then frozen (−80° C.) and thawed at RT, Cell lysates were suspended by pipetting several times and aliquots of 12.5 μL of each sample were transferred to a separate 96-well plate. 50 μL Luciferase substrate (LARII) was added to each extract and Firefly Luciferase activity was measured by Absorbance, Fluorescence and Luminescence Reader (Perkin Elmer, Victor™ 1240). 50 μL of Stop&Glo Reagent was added to each of the samples and Renilla Luciferase activity was measured immediately. Renilla Luciferase activity value was divided by Firefly Luciferase activity value for each sample (normalization) Renilla luciferase activity is finally expressed as the percentage of the normalized activity value in tested sample relative to the normalized value obtained in cells transfected with the corresponding psiCHECK™-2 plasmid in the absence of test or control molecules.

IC50 Calculation

The IC50 values of test and control molecule activity against the GS_CM site were determined by constructing a dose-response curve using the activity results obtained with the various final siRNA concentrations. The dose response curve was constructed by plotting the relative normalized values of Renilla luciferase activity versus the logarithm of transfected siRNA concentration. The curve was calculated by fitting the best sigmoid curve to the measured data. The methods for the sigmoid fit is called 3-point curve fit.

$$Y = Bot + \frac{100 - Bot}{1 + 10^{(LogIC50-X) \times HillSlope}}$$

Where:

Y is the residual caspase 2 mRNA response,

X is the logarithm of transfected siRNA concentration,

Bot is the Y value at the bottom plateau,

Log IC50 is the X value when Y is halfway between bottom and top plateaus and HillSlope is the steepness of the curve.

Results

For the evaluation of the potential off-target activity of each strand of a double stranded RNA molecule strands, the "guide-seed-sequence-and-passenger-strand-based activity assay" was employed using the psiCHECK (Promega) plasmid constructs. The measurement of Renilla activity provides a convenient way of monitoring double stranded RNA activity.

Measurement of Target Renilla Luciferase Protein Activity

The activity of both test and control molecules against the four target sequences (GS-CM, guide strand complete match; GS-SM, guide strand seed match; PS-CM, passenger strand complete match; and PS-SM, passenger strand seed match) was assessed at the protein level by measuring the relative activity of the Renilla luciferase reporter protein in cells transfected with various concentrations of molecule. Each assay was repeated three times. The IC50 value of test molecule activity against the GS-CM target site was determined by construction of concentration-response plots.

Both test and control molecules were active against the target GS-CM site in a dose response.

Both siRNAs were inactive against the GS-SM and the PS-SM sites.

FIGS. 2-10 and Tables 2-10 below show activity as measured by residual target for double stranded molecules targeting the complete match of a target sequence which has a substitution at position 19 (equivalent of position 1 of the antisense) to incorporate one of the ribonucleotides, adenosine (A or rA), cytidine (C or rC), guanosine (G or rG), ribothymidine (rT, also 5'methyluridine) and uridine (U or rU); or deoxyadenosine (dA), deoxycytidine (dC), deoxyguanosine (dG), thymidine (dT) and deoxyuridine (dU); or 2'O methylated adenosine (mA), 2'O methylated cytidine (mC), 2'O methylated guanosine (mG), 2'O methylated uridine (mU). "1st pos AS" refers to position 1 of the antisense strand (5' terminal nucleotide).

TABLE 2

TLR2_16 siRNA (blunt ended with alternating 2'-OMe on both strands)

| | | | 1st pos AS -mC | 1st pos AS -mG | 1st pos AS - mA | 1st pos AS - dU |
|---|---|---|---|---|---|---|
| siRNA concentration | 0.4 nM | Target G | 81 | 75 | 68 | 58 |
| | | Target U | 91 | 93 | 81 | 59 |
| | 4 nM | Target G | 85 | 61 | 50 | 38 |
| | | Target U | 84 | 78 | 56 | 40 |
| | 20 nM | Target G | 57 | 55 | 38 | 32 |
| | | Target U | 62 | 62 | 35 | 32 |

Figure 2:
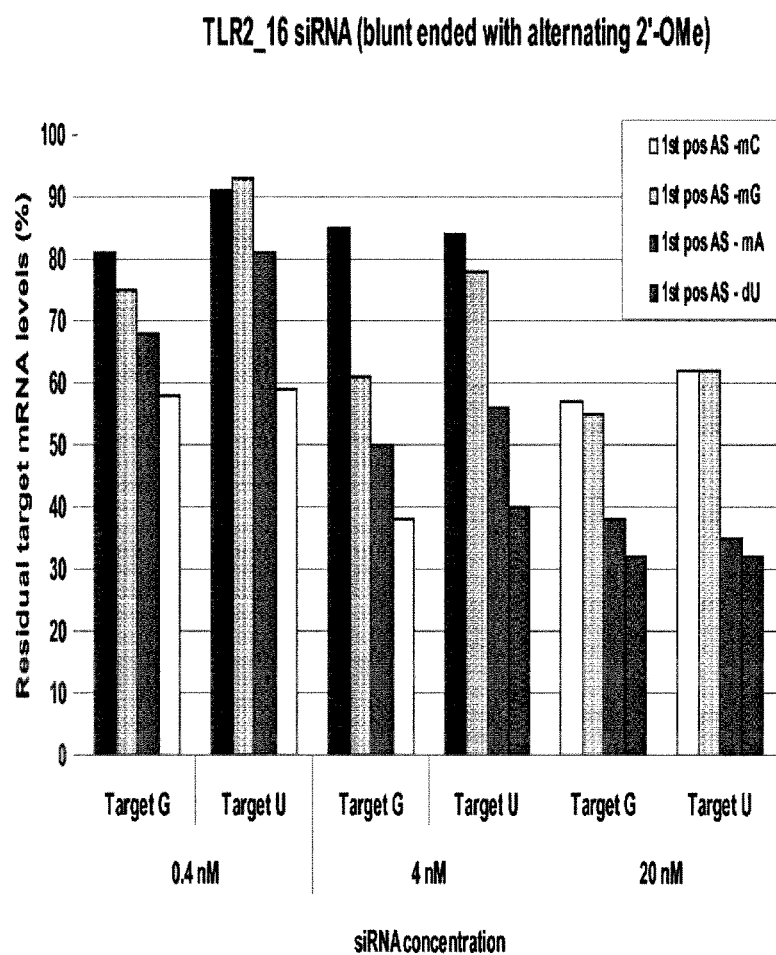
FIGS. 2-10 show activity (% residual target remaining) bar graphs of dsRNA molecules with different nucleotides in position 1 of the antisense strand to targets that have been modified to individually include the four ribonucleotides at position 19 (position 1 of AS).

The data shown in Table 2 is presented in FIG. 2. Methylated nucleotides at position 1 of the antisense strand show reduced target knockdown, irrespective of base pairing.

TABLE 3

TLR2_37 siRNA unmodified with C3-C3 overhangs or dTdT overhangs

| | | | dTdT overhang | C3-C3 overhang | | | | |
|---|---|---|---|---|---|---|---|---|
| | | Position 19 target | 1st pos AS -U | 1st pos AS -U | 1st pos AS - dU | 1st pos AS - dT | 1st pos AS - mU | 1st pos AS - A |
| siRNA concentration | 0.04 nM | Target A | 21 | 18 | 17 | 16 | 48 | 18 |
| | | Target C | 20 | 15 | 22 | 21 | 39 | 6 |
| | | Target G | 35 | 30 | 27 | 27 | 60 | 24 |
| | | Target U | 33 | 33 | 28 | 32 | 64 | 27 |
| | 0.4 nM | Target A | 13 | 8 | 8 | 9 | 23 | 11 |
| | | Target C | 12 | 9 | 9 | 11 | 18 | 10 |
| | | Target G | 17 | 13 | 12 | 13 | 34 | 16 |
| | | Target U | 19 | 17 | 12 | 16 | 43 | 14 |

TABLE 3-continued

TLR2_37 siRNA unmodified with C3-C3 overhangs or dTdT overhangs

| | Position 19 target | dTdT overhang 1st pos AS -U | C3-C3 overhang | | | | |
|---|---|---|---|---|---|---|---|
| | | | 1st pos AS -U | 1st pos AS - dU | 1st pos AS - dT | 1st pos AS - mU | 1st pos AS - A |
| 4 nM | Target A | 10 | 8 | 7 | 7 | 13 | 9 |
| | Target C | 8 | 7 | 8 | 9 | 12 | 10 |
| | Target G | 13 | 9 | 8 | 11 | 20 | 10 |
| | Target U | 12 | 13 | 8 | 9 | 22 | 12 |

Figure 3:
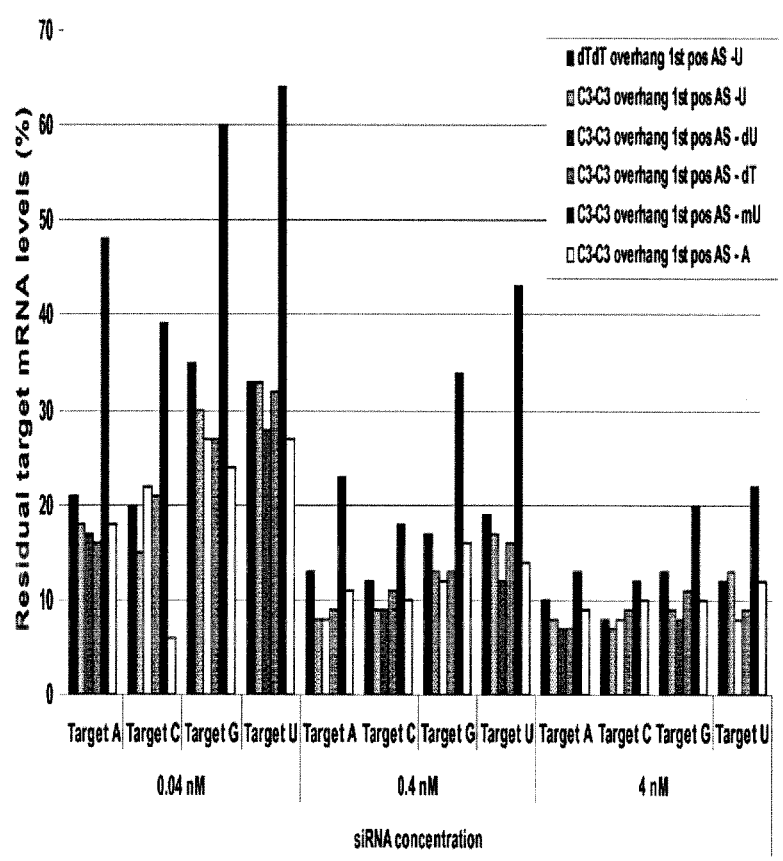

The data in Table 3 is presented in FIG. 3. Table 3 and FIG. 3 show that a 2'OMe ribonucleotide in the 1st position of AS reduces siRNA activity regardless of the nucleotide in the matching position of the target.

TABLE 4

TLR2_37 siRNA unmodified with C3-C3 overhangs or dTdT overhangs

| | | | dTdT overhang | C3-C3 overhang | | |
|---|---|---|---|---|---|---|
| | | | 1st pos AS -U | 1st pos AS -U | 1st pos AS - dU | 1st pos AS - dT |
| siRNA concentration | 0.04 nM | Target A | 21 | 18 | 17 | 16 |
| | | Target C | 20 | 15 | 22 | 21 |
| | | Target G | 35 | 30 | 27 | 27 |
| | | Target U | 33 | 33 | 28 | 32 |
| | 0.4 nM | Target A | 13 | 8 | 8 | 9 |
| | | Target C | 12 | 9 | 9 | 11 |
| | | Target G | 17 | 13 | 12 | 13 |
| | | Target U | 19 | 17 | 12 | 16 |

Figure 4:
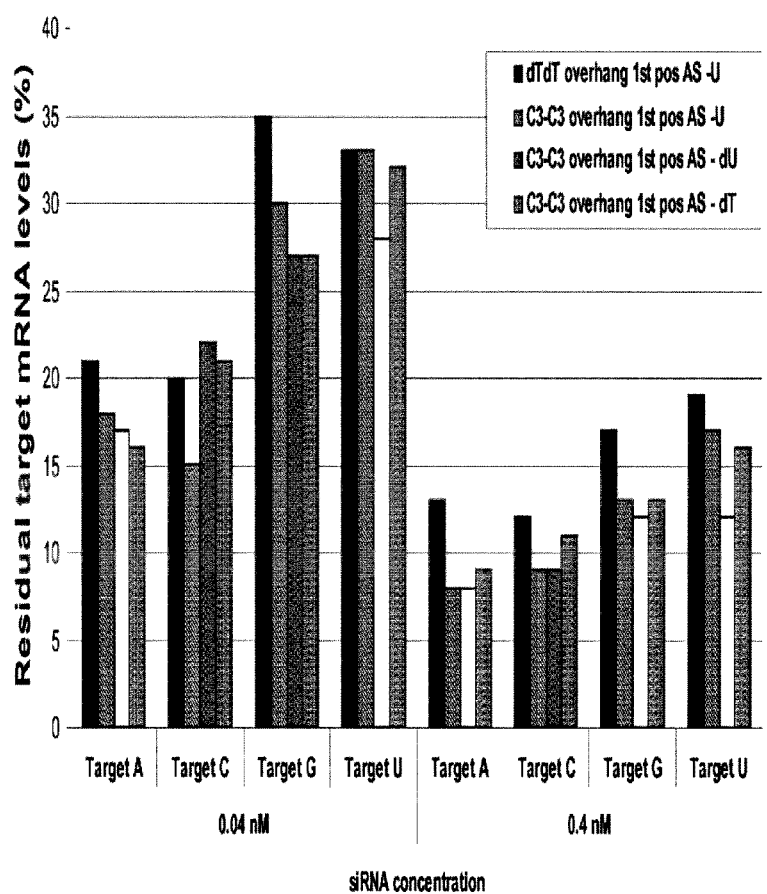

The data in Table 4 is presented in FIG. 4. Table 4 and FIG. 4 show that 1. siRNA with highest activity is observed when U (dU or dT) in the 1st position of AS is mismatched to C in the target or is matched to A in the target.
2. If U in the 1st position of AS of siRNA (or dU or dT) is mismatched to U in the target, siRNA activity is reduced
3. If U in the 1st position of AS is wobble-paired with G in target, siRNA activity is reduced.

TABLE 5

TLR2_37 siRNA (non-moditied with dTdT overhangs) - 0.04 nM

| | | | 1st pos AS - G | 1st pos AS - U |
|---|---|---|---|---|
| SiRNA concentration | 0.04 nM | Target A | 32 | 21 |
| | | Target C | 29 | 20 |
| | | Target G | 33 | 35 |
| | | Target U | 37 | 33 |
| | 0.4 nM | Target A | 14 | 13 |
| | | Target C | 13 | 12 |
| | | Target G | 17 | 17 |
| | | Target U | 21 | 19 |
| | 4 nM | Target A | 10 | 10 |
| | | Target C | 13 | 8 |
| | | Target G | 10 | 13 |
| | | Target U | 11 | 12 |
| | 20 nM | Target A | 9 | 11 |
| | | Target C | 8 | 8 |
| | | Target G | 8 | 11 |
| | | Target U | 10 | 11 |
| | 100 nM | Target A | 8 | 7 |
| | | Target C | 5 | 7 |
| | | Target G | 7 | 8 |
| | | Target U | 5 | 7 |

Figure 5:
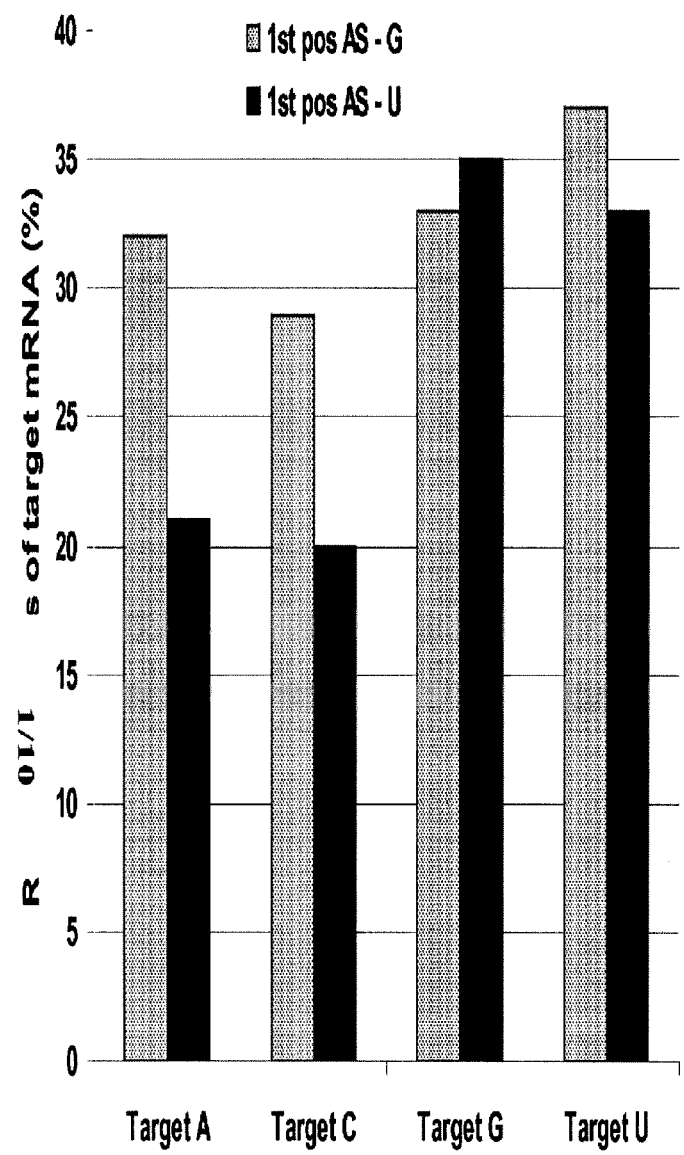

The data is Table 5 is presented in FIG. 5. Table 5 and FIG. 5 show that 1. U in the 1st position of the AS produced better results with its matched A or mismatched C in the target than with mismatched U or wobble-paired G.
2. G in the 1st position of the AS showed similar results with all possible nucleotides in the matching target position—mismatches or wobble-pairing did not improve activity.

TABLE 6

TLR2_46 siRNA (unmodified with C3-C3 or dTdT overhangs)

| | | | dTdT overhang | C3-C3 overhang | | | | |
|---|---|---|---|---|---|---|---|---|
| | | | 1st pos AS -U | 1st pos AS -U | 1st pos AS - dU | 1st pos AS - dT | 1st pos AS - mU | 1st pos AS - A |
| siRNA concentration | 0.04 nM | Target A | 70 | 83 | 61 | 69 | 79 | 52 |
| | | Target C | 56 | 78 | 49 | 66 | 85 | 58 |
| | | Target U | 68 | 85 | 57 | 69 | 95 | 67 |
| | 0.4 nM | Target A | 41 | 30 | 33 | 36 | 83 | 37 |
| | | Target C | 35 | 39 | 33 | 41 | 86 | 34 |
| | | Target U | 56 | 46 | 43 | 36 | 94 | 48 |
| | 4 nM | Target A | 13 | 16 | 17 | 20 | 39 | 14 |
| | | Target C | 15 | 17 | 11 | 24 | 48 | 13 |
| | | Target U | 19 | 21 | 17 | 14 | 59 | 19 |
| | 20 nM | Target A | 8 | 7 | 8 | 8 | 28 | 10 |
| | | Target C | 7 | 10 | 7 | 8 | 27 | 9 |
| | | Target U | 10 | 12 | 10 | 6 | 40 | 13 |

Figure 6:
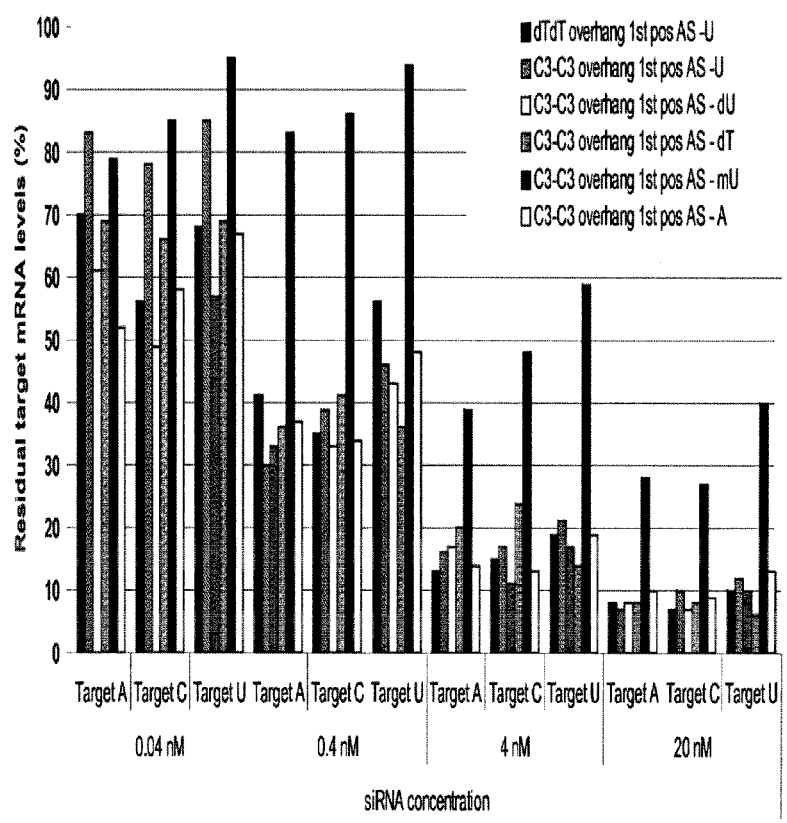

The data in Table 6 is presented in FIG. 6. Table 6 and FIG. 6 show that substitution of U with mU reduces activity

TABLE 7

| TLR2_46 siRNA (non-modified with dTdT overhangs) | | | | |
|---|---|---|---|---|
| | | | 1st pos AS - G | 1st pos AS - U |
| siRNA concentration | 0.4 nM | Target A | 53 | 41 |
| | | Target C | 61 | 35 |
| | | Target U | 68 | 56 |
| | 4 nM | Target A | 28 | 13 |
| | | Target C | 28 | 15 |
| | | Target U | 32 | 19 |
| | 20 nM | Target A | 16 | 8 |
| | | Target C | 15 | 7 |
| | | Target U | 17 | 10 |
| | 100 nM | target A | 16 | 8 |
| | | Target C | 15 | 7 |
| | | Target U | 17 | 10 |

Figure 7:
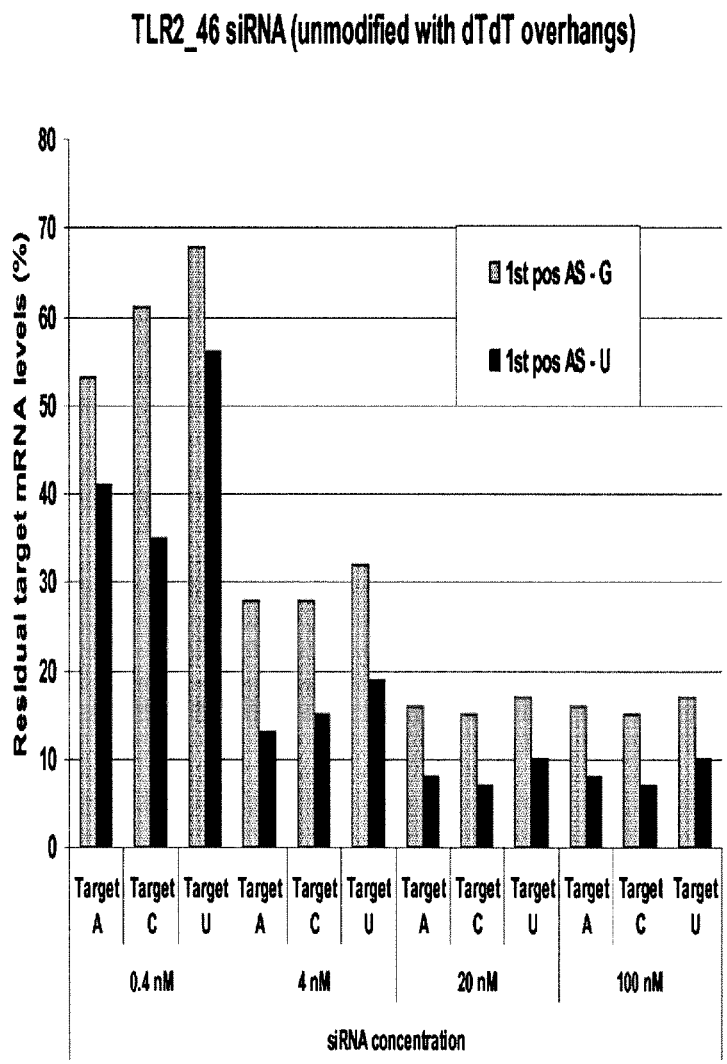

The data in Table 7 is presented in FIG. 7. Table 7 and FIG. 7 show that regardless of the nucleotide type of the matching target position, U in the 1st position of AS produced better KD (knock-down). All cases mean—regardless of the complementarity between siRNA and target in the 1st position of the guide strand, or mismatch or wobble pair.

TABLE 8

| RHOA_61 siRNA (non-modified/C3-C3 or dTdT overhangs) | | | | | | | | |
|---|---|---|---|---|---|---|---|---|
| | | | dTdT overhang | C3-C3 overhang | | | | |
| | | | 1st pos AS -U | 1st pos AS -U | 1st pos AS - dU | 1st pos AS - dT | 1st pos AS - mU | 1st pos AS - A |
| siRNA concentration | 0.04 nM | Target A | 35 | 50 | 34 | 33 | 76 | 33 |
| | | Target C | 32 | 38 | 33 | 32 | 86 | 34 |
| | | Target G | | 41 | | 51 | | 49 |
| | | Target U | | 53 | | 34 | | 36 |
| | 0.4 nM | Target A | 26 | 24 | 26 | 25 | 74 | 24 |
| | | Target C | 26 | 22 | | 22 | 66 | 23 |
| | | Target G | | 26 | 26 | 38 | | 35 |
| | | Target U | | 36 | | 27 | | 27 |
| | 4 nM | Target A | 22 | 22 | 24 | 17 | 37 | 20 |
| | | Target C | 18 | 19 | 21 | 17 | 34 | 18 |
| | | Target G | | 21 | | 31 | | 25 |
| | | Target U | | 30 | | 22 | | 22 |

Figure 8:
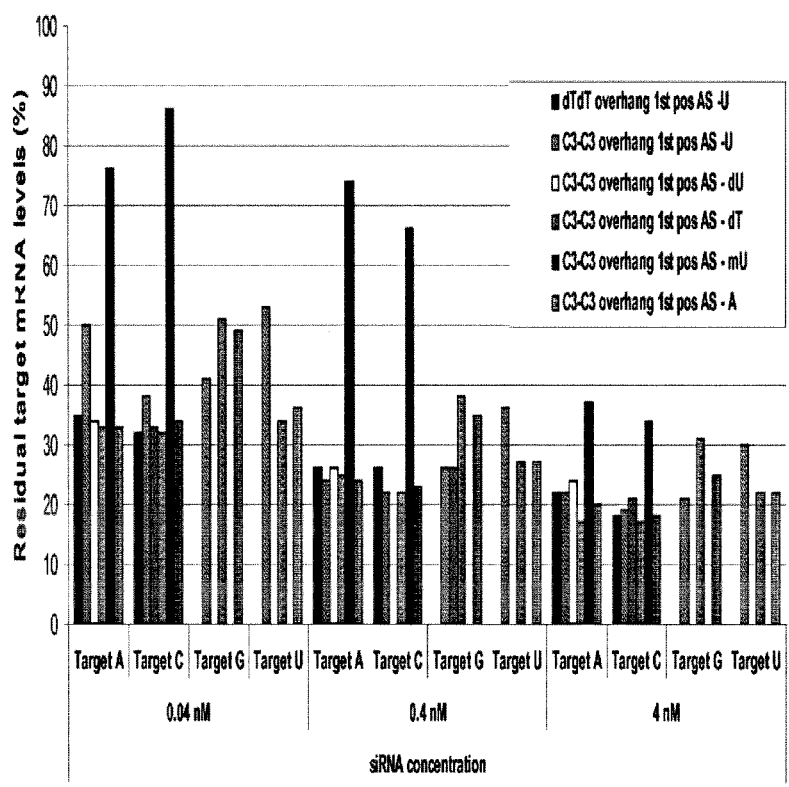

The data in Table 8 is presented in FIG. 8.

Figure 9:
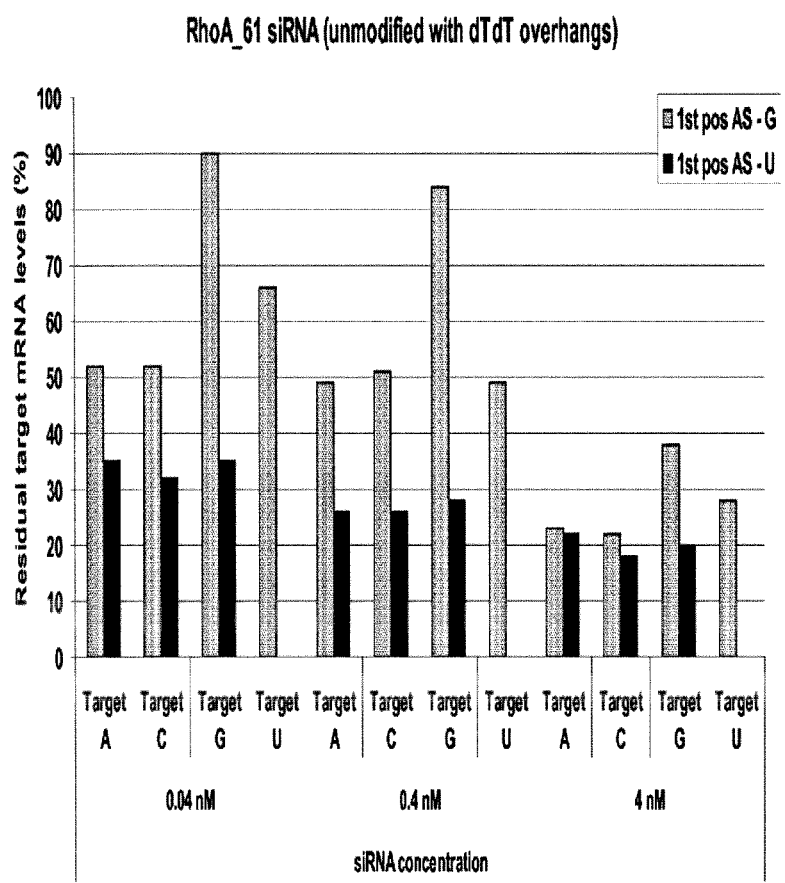

The data in Table 9 is presented in FIG. 9. Table 9 and FIG. 9 show that siRNAs with U in the 1st position of the AS are more active than those with G in the 1st position regardless of the nucleotide in the matching position of the target (match, mismatch, wobble). The results cannot be explained by Wobble base-pairing since having G in siRNA and U in the target is not equivalent to having U in siRNA and G in the target

TABLE 10

| RhoA_61 siRNA (unmodified with dTdT overhangs) | | | | |
|---|---|---|---|---|
| | | | 1st pos AS - G | 1st pos AS - U |
| siRNA concentration | 0.04 nM | Target A | 52 | 35 |
| | | Target C | 52 | 32 |
| | | Target G | 90 | |
| | | Target U | 66 | |
| | 0.4 nM | Target A | 49 | 26 |
| | | Target C | 51 | 26 |
| | | Target G | 84 | |
| | | Target U | 49 | |
| | 4 nM | Target A | 23 | 22 |
| | | Target C | 22 | 18 |
| | | Target G | 38 | |
| | | Target U | 28 | |

TABLE 9

| RHOA_61 siRNA (non-modified/C3-C3 or dTdT overhangs) | | | | | | | | |
|---|---|---|---|---|---|---|---|---|
| | | | dTdT overhang | C3-C3 overhang | | | | |
| | | | 1st pos AS -U | 1st pos AS -U | 1st pos AS - dU | 1st pos AS - dT | 1st pos AS - mU | 1st pos AS - A |
| siRNA concentration | 0.04 nM | Target A | 35 | 50 | 34 | 33 | 76 | 33 |
| | | Target C | 32 | 38 | 33 | 32 | 86 | 34 |
| | | Target G | | 41 | | 51 | | 49 |
| | | Target U | | 53 | | 34 | | 36 |
| | 0.4 nM | Target A | 26 | 24 | 26 | 25 | 74 | 24 |
| | | Target C | 26 | 22 | | 22 | 66 | 23 |
| | | Target G | | 26 | 26 | 38 | | 35 |
| | | Target U | | 36 | | 27 | | 27 |
| | 4 nM | Target A | 22 | 22 | 24 | 17 | 37 | 20 |
| | | Target C | 18 | 19 | 21 | 17 | 34 | 18 |
| | | Target G | | 21 | | 31 | | 25 |
| | | Target U | | 30 | | 22 | | 22 |

TABLE 10-continued

RhoA_61 siRNA (unmodified with dTdT overhangs)

|  |  | 1st pos AS - G | 1st pos AS - U |
|---|---|---|---|
| 20 nM | Target A | 21 | 20 |
|  | Target C | 18 | 17 |
|  | Target G | 29 |  |
|  | Target U | 21 |  |
| 100 nM | Target A | 18 | 19 |
|  | Target C | 19 | 16 |
|  | Target G | 25 |  |
|  | Target U | 20 |  |

Figure 10:
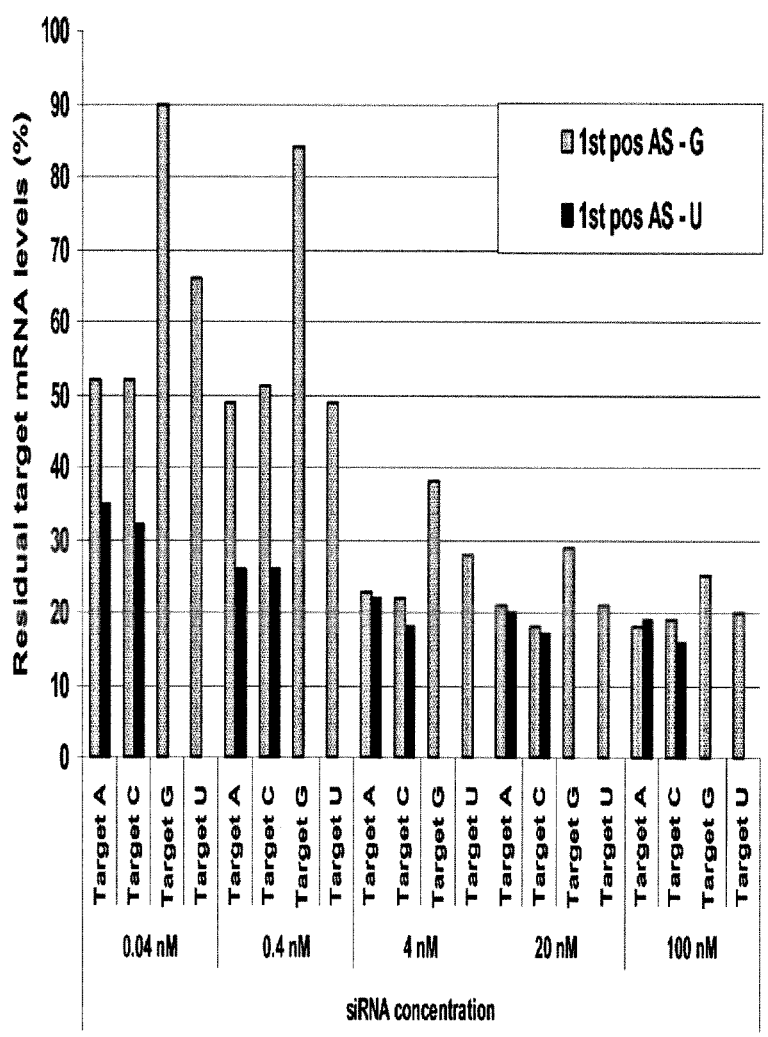

The data in Table 10 is presented in FIG. 10.

Example 3

Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine). Recent studies, support that apoptosis in renal tissues is prominent in most human oases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

The compounds of the invention are tested for efficacy in treating ischemia reperfusion injury in an animal model of ischemia-reperfusion-induced ARF.

Example 4

Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleol, and heels are especially susceptible; other sites may be involved depending on the patient's situation.

The compounds of the invention are tested for efficacy in treating pressure sores, ulcers and similar wounds in, inter alia, the mouse model as described in Reid et al., J Surg. Res. 116:172-180, 2004 or in the rabbit model as described by Mustoe et al, JCI, 1991. 87(2):694-703; Ahn and Mustoe, Ann Pl Surg, 1991. 24(1):17-23.

Example 5

Model Systems of Chronic Obstructive Pulmonary Disease (COPD)

Chronic obstructive pulmonary disease (COPD) is characterized mainly by emphysema, which is permanent destruction of peripheral air spaces, distal to terminal bronchioles. Emphysema is also characterized by accumulation of inflammatory cells such as macrophages and neutrophils in bronchioles and alveolar structures. Emphysema and chronic bronchitis may occur as part of COPD or independently.

The compounds of the invention are tested for efficacy in treating COPD/emphysema/chronic bronchitis in, inter alia, animal models such as those disclosed as follows:

Starcher and Williams, 1989. Lab. Animals, 23:234-240; Peng, et al., 2004.; Am J Respir Crit Care Med, 169:1245-1251; Jeyaseclan et al., 2004. Infect. Immunol, 72: 7247-56. Additional models are described in PCT patent publication WO 2006/023544 assigned to the assignee of the present application, which is hereby incorporated by reference into this application.

Example 6

Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

siRNA is injected into the spinal cord following spinal cord contusion and in uninjured rats. Sagittal cryosections are produced and immunostaining using four different groups of antibodies is performed in order to determine whether uptake has occurred in neurons, astroglia, oligdendmroglia and/or macrophages/microglia. Markers for neurons include NeuN, or GAP43; markers for astroglia and potential neural stem cells include GFAP, nestin or vimentin; markers for oligdendroglia include NG2 or APC; markers for macrophages/microglia include ED1 or Iba-1 (Hasegawa et al., 2005. Exp Neurol 193:394-410).

Rats are injected with two different doses of siRNA (1 µg/µl, 10 µg/µl) and are left for 1 and 3 days before sacrifice. The results indicate that siRNA to spinal cord injury target genes increases motoneuron recovery.

Example 7

Model Systems of Glaucoma

The compounds of the invention are tested for efficacy in treating or preventing glaucoma in the animal model, for example, as described by Pease at al., J. Glaucoma, 2006, 15(6):512-9 (Manometric calibration and comparison of TonoLab and TonoPen tonometers in rats with experimental glaucoma and in normal mice).

Example 7A

Model Systems of Ischemic Optic Neuropathy (ION)

An animal model for Ischemic optic neuropathy was established in adults Wistar rats using a protocol of optic nerve crush injury. Seven days prior to the optic nerve crush, the retinal ganglion cells (RGC) are selectively labelled by application of the retrograde tracer FluoroGold (2%, Fluorochrome, Englewood, Colo.) to the superior colliculus. The tracer is transported by retrograde transport along RGC axons resulting in complete and specific labelling of all RGCs within 1 week post injection of the fluorescent tracer. The animals are subjected to the optic nerve crush injury 7 days post retrograde tracing. The orbital optic nerve is exposed through a supraorbital approach and all axons in the optic nerve were transected by crushing with forceps for 10 seconds, 2 mm from the lamina eribrosa. A single dose of 20 µg/5 µl of PBS of the test modified siRNA compound is microinjected into the vitreous body 2 mm anterior to the nerve head, using a glass micropipette at the time of the optic nerve crush.

The survival of RGCs is determined 7 days following the optic nerve crush by counting FluoroGold-labelled RGCs on flat-mounted retinas. The experimental animals are perfused transcardially with 4% paraformaldehyde at 1 week after the optic nerve crush. Both retinas are dissected out, fixed for an additional 30 min and flat-mounted on a glass slide for ganglion cell layer quantification. The number of fluorescent RGCs is counted in 16 distinct areas in each retina and the percent of survival of the RGCs is determined compared to samples obtained from rats which did not undergo optic nerve crush injury at all or samples obtained from rats which were injected with PBS, control siRNA or GFP siRNA along with the optic nerve crush injury. Microglia cells that may have incorporated FluoroGold after phagocytosis of dying RGCs were distinguished by their characteristic morphology and excluded from quantitative analyses.

Another model of optic nerve axotomy where the entire population of RGCs are axotomized by transecting the optic nerve close to the eye is utilized. (Cheng L, et al. *J. Neurosci.* 2002; 22:3977-3986).

Example 8

Model Systems of Ischemia/Reperfusion Injury Following Lung Transplantation in Rats The compounds of the invention are tested for efficacy in treating ischemia/reperfusion injury or hypoxic injury following lung transplantation in one or more of the experimental animal models, for example as described by Mizobuchi et al., 2004. J. Heart Lung Transplant, 23:889-93; Huang, et al., 1995. J. Heart Lung Transplant. 14: 849; Matsumura, et al., 1995. Transplantation 59: 1509-1517; Wilkes, et al., 1999. Transplantation 67:890-896; Naka, et al., 1996. Circulation Research, 79: 773-783.

Example 9

Model Systems of Acute Respiratory Distress Syndrome

The compounds of the invention are tested for efficacy in treating acute respiratory distress syndrome in inter alia in the animal model described by Chen et al (J Biomed Sci. 2003; 10(6 Pt 1):588-92. Modified siRNA compounds that target genes including CYBA, IRK, BNIP3, MAPK8, MAPK14, RAC1, GSK3B, P2RX7, TRPM2, PARG, SPP1, and DUOX1 are tested in this animal model.

Example 10

Model Systems of Hearing Loss Conditions (i) Chinchilla Model of Carboplatin-Induced or Cisplatin-Induced Cochlea Hair Cell Death Chinchillas are pre-treated by direct administration of specific siRNA in saline to the left car of each animal. Saline is given to the right ear of each animal as placebo. Two days following the administration of the specific modified siRNA compounds of the invention, the animals are treated with carboplatin (75 mg/kg ip) or cisplatin (intraperitoneal infusion of 13 mg/kg over 30 minutes). After sacrifice of the chinchillas (two weeks post carboplatin treatment) the % of dead cells of inner hair cells (IHC) and outer hair cells (OHC) is calculated in the left ear (siRNA treated) and in the right ear (saline treated). It is calculated that the % of dead cells of inner hair cells (IHC) and outer hair cells (OHC) is lower in the left ear (siRNA treated) than in the right ear (saline treated).

(ii) Chinchilla Model of Acoustic-Induced Cochlea Hair Cell Death

The activity of specific siRNA in an acoustic trauma model is studied in chinchilla. The animals are exposed to an octave band of noise centered at 4 kHz for 2.5 h at 105 dB. The left car of the noise-exposed chinchillas is pre-treated (48 h before the acoustic trauma) with 30 µg of siRNA in ~10 µL of saline; the right ear is pre-treated with vehicle (saline). The compound action potential (CAP) is a convenient and reliable clcctrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (saline) ear. In addition, the level of inner and outer hair cell loss is determined in the siRNA-treated and the control ear.

Similar models are used in mice and rats. The modified siRNA compounds that target genes including BNIP3, CAPNS, HES1, HES5, NOX3, ID1-3, HRK, ASPP2 (TP53BP), CASP2, RAC1, HTRA2, CDKN1B are tested in these and other animal model of hearing loss and hearing regeneration.

Example 11

Animal Models of Osteoarthritis (OA)

Collagen induced arthritis (CIA): CIA in mice is described in Trentham et al. (1977. J. Exp. Med, 146: 857-868). Adjuvant-induced arthritis (AA):AA is described in Kong ct al., (1999. Nature, 402:304-308). A menisectomy model is described in Han et al., (1999. Nagoya J Med Sci 62(3-4):115-26).

The effect of different siRNA inhibitors, such as siRNA to SSP1, on different parameters related to OA such as chondrocyte proliferation, terminal differentiation and development of arthritis, is evaluated using one or more of the above models, in addition to in vitro models known in the art. Modified siRNA compounds directed to proapoptotic genes, in particular to SSP1, are tested in these animal models which show that the modified siRNA compounds treat and/or prevent OA and thus may be used to treat this condition.

Example 12

Rat Model Systems for Transplantation-Associated Acute Kidney Injury

Warm Ischemia—In test rats a left nephrectomy is performed, followed by auto transplantation that results in a warm kidney graft preservation period of 45 minutes. Following auto transplantation, a right nephrectomy is performed on the same animal. Chemically modified siRNA to a target is administered intravenously via the femoral vein either before harvesting of the kidney graft (mimicking donor treatment) ("pre"), or after the kidney autotransplantation (mimicking recipient treatment), or both before harvest and after transplantation (combined donor and recipient treatment) ("pre-post").

Cold Ischemia—A left nephrectomy is performed on a donor animal, followed by a cold preservation (on ice) of the harvested kidney for a period of 5 hours. At the end of this period, the recipient rat will undergo a bilateral nephrectomy, followed by transplantation of the cold-preserved kidney graft. The total warm ischemia time (including surgical procedure) is about 30 minutes. Chemically modified siRNA is administered intravenously via the femoral vein, either to the donor animal prior to the kidney harvest ("pre"), or to the recipient animal 15 minutes ("post 15 min") or 4 hours (post 4 hrs) post-transplantation.

To assess the efficacy of the modified siRNA compounds of the present invention in improving post-transplantation renal function, serum creatinine levels are measured on days 1, 2, and 7 post-transplantation in both warm and cold ischemia models.

Those skilled in the art will recognize, or be able to ascertain using no more than routine experimentation, equivalents of the specific embodiments of the invention described herein. Such equivalents are intended to be encompassed by the following claims.

The invention claimed is:

1. A double-stranded nucleic acid having structure (A) set forth below:

(A)
5'    $N^1$-(N)x - Z 3' (antisense strand)

3' Z'-$N^2$-(N')y-z" 5' (sense strand)

wherein each of $N^2$, N and N' is an unmodified ribonucleotide, a modified ribonucleotide, or an unconventional moiety;
wherein each of (N)x and (N')y is an oligonucleotide in which each consecutive N or N' is joined to the adjacent N or N' by a covalent bond;
wherein x=y=18;
wherein the sequence of $N^2$-(N')y is fully complementary to the sequence of $N^1$-(N)x and the sequence of (N)x has complementarity to a consecutive sequence in a target RNA;
wherein $N^1$ is covalently bound to (N)x and not complementary to the corresponding nucleotide in the target RNA or is an unconventional moiety complementary to the target RNA;
wherein:
$N^1$ is selected from the group consisting of a modified adenosine and a modified deoxyadenosine when the corresponding nucleotide in the target RNA sequence is adenosine; or
$N^1$ is selected from the group consisting of a modified adenosine, a modified deoxyadenosine and a modified deoxythymidine when the corresponding nucleotide in the target RNA sequence is cytidine; or N¹ is selected from the group consisting of a modified adenosine, a modified deoxyadenosine and a modified deoxythymidine when the corresponding nucleotide in the target RNA sequence is guanosine; or N¹ is selected from the group consisting of a modified uridine and a modified deoxyuridine when the corresponding nucleotide in the target RNA sequence is uridine;

wherein z" may be present or absent, but if present is a capping moiety covalently attached at the 5' terminus of N²-(N')y; and wherein each of Z and Z' is independently present or absent, but if present is independently 1-5 consecutive nucleotides, 1-5 consecutive non-nucleotide moieties or a combination of 1-5 nucleotides and non-nucleotide moieties, covalently attached at the 3' terminus of the strand in which it is present;

or a pharmaceutically acceptable salt of the double stranded nucleic acid.

2. A double-stranded nucleic acid having structure (A) set forth below:

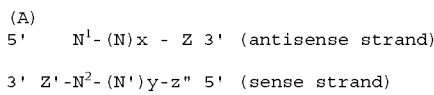

wherein each of N², N and N' is an unmodified ribonucleotide, a modified ribonucleotide, or an unconventional moiety;

wherein each of (N)x and (N')y is an oligonucleotide in which each consecutive N or N' is joined to the adjacent N or N' by a covalent bond;

wherein x=y=18;

wherein the sequence of N²-(N')y is fully complementary to the sequence of N¹-(N)x and the sequence of (N)x has complementarity to a consecutive sequence in a target RNA;

wherein N¹ is covalently bound to (N)x and not complementary to the corresponding nucleotide in the target RNA or is an unconventional moiety complementary to the target RNA;

wherein N¹ is a modified adenosine and the corresponding nucleotide in the target RNA is adenosine;

wherein z" may be present or absent, but if present is a capping moiety covalently attached at the 5' terminus of N²-(N')y; and wherein each of Z and Z' is independently present or absent, but if present is independently 1-5 consecutive nucleotides, 1-5 consecutive non-nucleotide moieties or a combination of 1-5 nucleotides and non-nucleotide moieties, covalently attached at the 3' terminus of the strand in which it is present;

or a pharmaceutically acceptable salt of the double stranded nucleic acid.

3. The double-stranded nucleic acid of claim 2, wherein N¹ is a 2'O-methyl sugar modified adenosine.

4. The double-stranded nucleic acid of claim 1, wherein z" is present.

5. The double-stranded nucleic acid of claim 1, wherein Z and Z' are absent.

6. The double-stranded nucleic acid of claim 1, wherein one of Z or Z' is present.

7. The double-stranded nucleic acid of claim 6, wherein Z or Z' comprise non-nucleotide moieties.

8. The double-stranded nucleic acid of claim 1, wherein at least one of N or N' comprises a 2'O-methyl sugar-modified ribonucleotide.

9. The double-stranded nucleic acid of claim 8, wherein (N)x comprises 2'O-methyl sugar-modified ribonucleotides.

10. The double-stranded nucleic acid of claim 1, wherein the double-stranded nucleic acid is a siRNA, siNA or a miRNA.

11. A double-stranded nucleic acid having structure (A) set forth below:

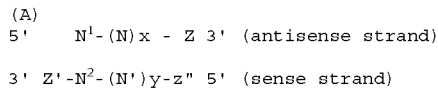

wherein N, N', (N)x, (N')y, x, y, Z' and z" are as defined in claim 2;

wherein the sequence of N²-(N')y is fully complementary to the sequence of N¹-(N)x and the sequence of (N)x has complementarity to a consecutive sequence in a target RNA;

wherein N¹ is covalently bound to (N)x and not complementary to the corresponding nucleotide in the target RNA or is an unconventional moiety complementary to the target RNA;

wherein Z' is absent or present, Z is present and comprises two alkyl moieties covalently linked to each other via a phosphodiester bond, wherein N² comprises uridine or deoxyuridine; and wherein N¹ comprises adenosine when the corresponding nucleotide in the target RNA is adenosine, guanosine or cytidine;

or a pharmaceutically acceptable salt of the double stranded nucleic acid.

12. The double-stranded nucleic acid of claim 1, wherein the target RNA is an mRNA encoded by a mammalian gene.

13. The double-stranded nucleic acid of claim 12, wherein the target mRNA is an mRNA encoded by a human gene.

14. A composition comprising at least one double-stranded nucleic acid or a pharmaceutically acceptable salt of such double-stranded nucleic acid of claim 1; and a pharmaceutically acceptable carrier.

15. A method for treating or preventing the incidence or severity of a disease or condition in a subject in need thereof, comprising administering to the subject a double-stranded nucleic acid of claim 1 in an amount effective to prevent or treat or delay the onset of the disease or the condition, wherein the disease or the condition and/or symptoms associated therewith is selected from the group consisting of hearing loss, acute renal failure (ARF), Delayed Graft Function (DGF) after kidney transplantation, glaucoma, ocular ischemic conditions, including non-arteric ischemic optic neuropathy (NAION), anterior ischemic optic neuropathy, age-related macular degeneration (AMD), Ischemic Optic Neuropathy (ION) and dry eye syndrome, acute respiratory distress syndrome (ARDS) and other acute lung and respiratory injuries, chronic obstructive pulmonary disease (COPD), primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, organ transplantation including lung, liver, heart, pancreas, and kidney transplantation, nephro- and neurotoxicity, spinal cord injury, brain injury, neurodegenerative disease or condition, pressure sores, oral mucositis, fibrotic disorders and cancer.

16. A double-stranded nucleic acid molecule having structure (A) set forth below:

```
(A)
5'    N¹-(N)x - Z 3'  (antisense strand)

3' Z'-N²-(N')y-z" 5'  (sense strand)
``` wherein N², N, N', (N)x, (N')y, x, y, Z, Z' and z" are as defined in claim 2;

wherein the sequence of N²-(N')y is fully complementary to the sequence of N¹-(N)x and the sequence of (N)x has complementarity to a consecutive sequence in a target RNA;

wherein N¹ is covalently bound to (N)x and not complementary to the corresponding nucleotide in the target RNA or is an unconventional moiety complementary to the target RNA;

wherein N¹ is selected from the group consisting of a modified adenosine, a modified deoxyadenosine and a modified deoxythymidine, when the corresponding nucleotide in the target RNA is cytidine;

or a pharmaceutically acceptable salt of the double stranded nucleic acid.

17. A double-stranded nucleic acid molecule having structure (A) set forth below:

```
(A)
5'    N¹-(N)x - Z 3'  (antisense strand)

3' Z'-N²-(N')y-z" 5'  (sense strand)
``` wherein N², N, N', (N)x, (N')y, x, y, Z, Z' and z" are as defined in claim 2;

wherein the sequence of N²-(N')y is fully complementary to the sequence of N¹-(N)x and the sequence of (N)x has complementarity to a consecutive sequence in a target RNA;

wherein N¹ is covalently bound to (N)x and not complementary to the corresponding nucleotide in the target RNA or is an unconventional moiety complementary to the target RNA;

wherein N¹ is selected from the group consisting of a modified adenosine, a modified deoxyadenosine and a modified deoxythymidine when the corresponding nucleotide in the target RNA is guanosine;

or a pharmaceutically acceptable salt of the double stranded nucleic acid.

18. A double-stranded nucleic acid molecule having structure (A) set forth below:

```
(A)
5'    N¹-(N)x - Z 3'  (antisense strand)

3' Z'-N²-(N')y-z" 5'  (sense strand)
``` wherein N², N, N', (N)x, (N')y, x, y, Z, Z' and z" are as defined in claim 2;

wherein the sequence of N²-(N')y is fully complementary to the sequence of N¹-(N)x and the sequence of (N)x has complementarity to a consecutive sequence in a target RNA;

wherein N¹ is covalently bound to (N)x and not complementary to the corresponding nucleotide in the target RNA or is an unconventional moiety complementary to the target RNA;

wherein N¹ is a modified uridine or a modified deoxyuridine, when the corresponding nucleotide in the target RNA is uridine;

or a pharmaceutically acceptable salt of the double stranded nucleic acid.

* * * * *